(12) United States Patent
Riordan

(10) Patent No.: US 8,076,101 B2
(45) Date of Patent: Dec. 13, 2011

(54) METHOD OF DETECTING THE CYSTIC FIBROSIS TRANSMEMBRANE CONDUCTANCE REGULATOR (CFTR) AT CELL EXTERIOR

(76) Inventor: John R. Riordan, Chapel Hill, NC (US)

( * ) Notice: Subject to any disclaimer, the term of this patent is extended or adjusted under 35 U.S.C. 154(b) by 788 days.

(21) Appl. No.: 10/554,770

(22) PCT Filed: May 20, 2004

(86) PCT No.: PCT/US2004/018475
§ 371 (c)(1),
(2), (4) Date: Sep. 25, 2006

(87) PCT Pub. No.: WO2005/003720
PCT Pub. Date: Jan. 13, 2005

(65) Prior Publication Data
US 2007/0243555 A1    Oct. 18, 2007

Related U.S. Application Data

(60) Provisional application No. 60/472,267, filed on May 21, 2003.

(51) Int. Cl.
C12N 15/00    (2006.01)
C12N 15/09    (2006.01)
C12N 5/00     (2006.01)
C07H 21/00    (2006.01)

(52) U.S. Cl. .................... 435/69.1; 435/325; 435/320.1; 536/23.1

(58) Field of Classification Search .................. None
See application file for complete search history.

(56) References Cited

U.S. PATENT DOCUMENTS

| | | | |
|---|---|---|---|
| 5,543,399 A | 8/1996 | Riordan et al. | |
| 5,776,677 A | 7/1998 | Tsui et al. | |
| 5,888,722 A * | 3/1999 | Costa De Beauregard et al. | ................... 435/4 |
| 6,201,107 B1 | 3/2001 | Lap-Chee et al. | |
| 6,303,373 B1 * | 10/2001 | Bogan et al. | ................... 435/325 |
| 6,730,777 B1 | 5/2004 | Tsui et al. | |
| 6,902,907 B1 | 6/2005 | Tsui et al. | |
| 6,984,487 B1 | 1/2006 | Tsui et al. | |

OTHER PUBLICATIONS

Kaufman et al. Transgenic analysis of a 100-kb human B-globin cluster-containing DNA fragment propagated as a bacterial artificial chromosome. Blood 94: 3178-3184 (1999).*
Wigley et al. Site-specific transgene insertion: an approach. Reprod Fertil Dev 6:585-588 (1994).*
Phillips, A. The challenge of gene therapy and DNA delivery. J Pharm Pharmacology 53:1169-1174 (2001).*
Howard et al. cAMP regulated trafficking of epitope-tagged CFTR. Kidney International vol. 49:1642-1648 (1996).*
Howard et al. Epitope tagging permits cell surface detection of functional CFTR. Am J. Physiol (Cell) 269:C1565-C1576 (1995).*
Wells, J.A. Additivity of Mutational Effects in Proteins. Biochemistry 29:8509-8517 (1990).*
Ngo et al. Computational Complexity, Protein Structure Prediction and the Levinthal Paradox. The Protein Folding Problem and Tertiary Structure Prediction, pp. 433-440 and 492-495; (1994).*
Riordan JR et al. Identification of the cystic fibrosis gene: closing and characterization of complementary DNA. Science. Sep. 8, 1989; 245(4922): 1066-1073.
Seibert FS et al. Cytoplasmic loop three of cystic fibrosis transmembrane conductance regulator contributes to regulation of chloride channel activity. The Journal of Biological Chemistry. Nov. 1, 1996; 271(44): 27493-27499.
Peters KW et al. Syntaxin 1A inhibits regulated CFTR trafficking in *Xenopus oocytes*. Am. J. Physiol. 277 (Cell Physiol. 46). 1999: C174-C180.
Gentzsch M et al. Endocytic trafficking routes of wild type and ΔF508 cystic fibrosis transmembrane conductance regulator. Molecular Biology of the Cell. Jun. 2004; 15: 2684-2696.

* cited by examiner

*Primary Examiner* — Bridget E Bunner
*Assistant Examiner* — Regina M Deberry
(74) *Attorney, Agent, or Firm* — Myers Bigel Sibley & Sajovec, P.A.

(57) ABSTRACT

The present invention provides a recombinant nucleic acid encoding a modified cystic fibrosis transmembrane conductance regulator (CFTR) protein. The nucleic acid is modified by the insertion of a first heterologous segment encoding a detectable epitope in a region encoding an extracytoplasmic loop, such as at least one of EL1 through EL6. E12 is currently preferred. Proteins encoded by such nucleic acids, vectors and cells containing such nucleic acids, and methods of use thereof are also described.

13 Claims, 13 Drawing Sheets

*(1) Sequences of 6 extracytoplasmic loops (N-glycosylation sites in EL4 are in bold)*

EL1: GRIIA<u>SYDPDN</u>KEER (SEQ ID NO: 19)

EL2: WELLQ (SEQ ID NO: 20)

EL3: K

EL4: LWLLGNTPLQD*KGNSTHSRNNSYAVIIT*STS (SEQ ID NO: 21)

EL5: QP

EL6: EGEGR (SEQ ID NO: 22)

*(2) Insertion of underlined portion of EL1 and italic portion of EL4 into EL2 and EL6:*

EL2': WELNT<u>SYDPDN</u>*KGNTSHSRNNSYAVIITS*<u>KEER</u>SLQ (SEQ ID NO: 23)

EL6': EGENT<u>SYDPDN</u>*KGNTSHSRNNSYAVIITS*<u>KEER</u>SGR (SEQ ID NO: 24)

*(3) Replacement of central overlined 5 residues with 9 residue HA epitope (highlighted in bold):*

XT-EL2': WELNT<u>SYDPDN</u>*KGNT*YPYDVPDYAN*SYAYIITS*<u>KEER</u>SLQ (SEQ ID NO: 25)

XT-EL6': EGENT<u>SYDPDN</u>*KGNT*YPYDVPDYAN*SYAVIITS*<u>KEER</u>SGR (SEQ ID NO: 26)

Figure 1C

METHOD OF DETECTING THE CYSTIC FIBROSIS TRANSMEMBRANE CONDUCTANCE REGULATOR (CFTR) AT CELL EXTERIOR

RELATED APPLICATIONS

The present application is a National Phase Application of International Application Serial No PCT/US2004/018475, filed May 20, 2004, which in turn claims the benefit of Provisional Application Ser. No. 60/472,267; Filed May 21, 2003, the disclosures of which are hereby incorporated herein by reference in their entirety.

FIELD OF THE INVENTION

The present invention provides a method of detection of the cystic fibrosis transmembrane conductance regulator (CFTR) at the exterior of the cell, a high throughput screen for agents that promote transport to the cell surface plasma membrane of Δ508 CFTR and other misprocessed disease-associated CFTR mutants. The method of specifically labeling only the cell surface CFTR pool also enables its endocytosis and turnover to be quantified and thereby to also screen for agents that stabilize this pool.

BACKGROUND OF THE INVENTION

The CFTR protein exposes only ~3% of its mass on the exterior surface of the plasma membrane making its detection difficult without permeabilization of the membrane. After the CFTR amino acid sequence and predicted 2D membrane topology became available (Riordan et al., 1989) extensive efforts were made to raise antibodies that would recognize epitopes within the extracytoplasmic loops (ELs) and some success was reported (Denning et al., 1992). However, both this study, where polyclonal antisera were generated against a synthetic peptide corresponding to the sequence of the first EL, and other work at Transgene S.A. where monoclonal antibodies were generated against a similar peptide, were never confirmed or shown to be of practical use in the ensuing decade. Efforts in several other laboratories to generate EL1 antibodies capable of detecting CFTR from the cell exterior were unsuccessful.

A somewhat more successful approach was taken by Howard and coworkers (Howard et al., 1995; Howard et al., 1996; Schultz et al., 1997) who inserted exogenous epitopes in the fourth extracytoplasmic loop (EL4). However in so doing the native N-glycosylation sites at asparagine residues 894 and 900 were removed so that only unglycosylated CFTR could be detected at the cell surface. Although it is known that unglycosylated CFTR is transported to the cell surface where it has some chloride channel activity, it is also known that it is expressed poorly compared to the native glycosylated molecule and has a much shorter lifetime. Therefore it is not useful to monitor conditions that would favor transport of the ΔF508 CFTR polypeptide to the cell surface. Introduction of an epitope into EL4 has also been referred to in some more recent publications (Konstas et al., 2002; Benharouga et al., 2003). However, no details of how this was done were provided and results were shown only for *Xenopus* oocytes and not in a cell system amenable to high throughput screening (Konstas et al., 2002). It is not known whether or not this EL4 epitope insertion enables only detection of unglycosylated CFTR, as was the case with the earlier EL4 insertion (Howard et al., 1995).

Approximately 90% of CF patients have the ΔF508 mutation at at least one CFTR allele (Drumm and Collins, 1993). The deletion of this single amino acid prevents the nascent protein from maturing conformationally and being transported to its site of action at the cell surface plasma membrane (reviewed in Riordan, 1999; Kopito, 1999; Gelman and Kopito, 2002). The latter article emphasizes that the search for small molecules that either circumvent or overcome this defect is a vitally important approach to the discovery of new therapeutics for the disease.

SUMMARY OF THE INVENTION

The present invention provides a recombinant nucleic acid encoding a modified cystic fibrosis transmembrane conductance regulator (CFTR) protein. The nucleic acid is modified by the insertion of a first heterologous segment encoding a detectable epitope in a region encoding an extracytoplasmic loop, such as at least one of the first, second, third, fourth, fifth or sixth extracytoplasmic loops (EL1, EL2, EL3, EL4, EL5, or EL6). EL2 is currently preferred. The first heterologous segment may be flanked on either, or preferably both, sides by regions encoding additional second and third heterologous segments.

A second aspect of the present invention is a protein encoded by a recombinant nucleic acid as described herein.

A third aspect of the present invention is a vector comprising a recombinant nucleic acid as described herein, which recombinant nucleic acid may be operably associated with a promoter.

A further aspect of the present invention is a cell (e.g., a mammalian cell or other eukaryotic cell) that contains a recombinant nucleic acid as described herein (which cell in some embodiments expresses the encoded protein).

A further aspect of the present invention is a method of screening compounds for activity in promoting, facilitating, increasing or enhancing the transport of the cystic fibrosis transmembrane conductance regulator protein to the cell surface utilizing cells that contain and express the recombinant nucleic acids described herein.

A further aspect of the present invention is a method of treating cystic fibrosis by administering to an afflicted subject, typically a human subject, a compound which compound can be identified by a screening method as described herein.

The forgoing and other objects and aspects of the present invention are explained in greater detail in the drawings herein and the specification set forth below.

BRIEF DESCRIPTION OF THE DRAWINGS

FIG. 1. Strategy and methods to provide an exposed epitope tag in the second extracytoplasmic loop (EL2) of CFTR.

FIG. 1C. Amino acid sequence changes involved in modification of extracytoplasmic loops EL2 or EL6 to provide exposed epitope tag (Extope-CFTR).

FIG. 2A. Wild-type CFTR (WT) with EL2 modified to include exposed epitope (XT) in first lane and similarly modified ΔF508 CFTR in second lane. Arrowhead indicates mature protein, arrow immature.

FIG. 2B. Wild-type CFTR (WT) in first lane and ΔF508 CFTR with modified EL2 (XT-ΔF) in lane 2 (growth at 28° C.) and 3 (growth at 28° C. in 2 mM sodium butyrate). Arrowhead indicates mature protein, arrow immature.

FIG. 2C. N-glycanase digestion of ΔF508 CFTR with modified EL2 after growth at 28° C. with 2 mM sodium butyrate converts mature (arrowhead) and immature (solid arrow) to unglycosylated protein (open arrow).

FIG. 8A. Cell surface pools of Extope-CFTR are internalized. BHK-21 cells stably expressing Extope-CFTR were pre-cooled and cell surface pools of Extope CFTR were labeled for 30 minutes on ice with mouse monoclonal anti-HA Ab 16B12. Cells were then washed with ice-cold PBS and reincubated for the indicated times. Bars, 10 μm.

FIG. 8B. Internalized pools of CFTR are rapidly recycled. Cells were labeled for 10 minutes with monoclonal mouse anti-HA antibody 12CA5 and then washed with PBS pH 3.7 to remove antibody from the cell surface. Reincubation in pre-warmed media for different times results in re-appearance of CFTR at the cell edges. Cells were fixed with 4% paraformaldehyde for 10 minutes and permeabilized with 0.1% saponin in PBS. Extope-CFTR labeled with 12CA5 mAb was detected with goat anti-mouse IgG conjugated to Alexa Fluor 488. Nuclei were stained with propidium iodide.

FIG. 8C. Recycled CFTR is re-directed to the cell surface. Internalized Extope-CFTR is detectable at the cell surface of non-permeablized cells after 5 minutes reincubation in media. Extope-CFTR expressing cells were labeled with 12CA5 and washed to remove external label as in FIG. 2B. Cells were fixed immediately or after 5 minutes reincubation in warm media and either not permeabilized (NP) or permeabilized (P). Extope-CFTR labeled with 12CA5 mAb was immunostained by goat anti-mouse IgG conjugated to Alexa Fluor 488.

FIG. 8D. Quantification of CFTR recycling to the plasma membrane. The internalized pool of CFTR is almost completely redirected to the cell surface in 5 minutes. Experiments were performed as in FIG. 2C and mean green fluorescence per cell was determined as described in Methods using ImageJ 1.30v software. Each point represents the average of at least 10 cells and standard deviations are indicated.

FIG. 9A. Extope-ΔF508 CFIR matures at low temperature. Cells expressing Extope-CFTR and Extope-ΔF508 CFTR were grown at 37° C. or at 27° C. in the presence of 2 mM butyrate to increase expression and cell lysates were analyzed by immunoblotting as described in FIG. 1B using anti-CFTR antibody 596.

FIG. 9B. Localization of Extope-CFTR and Extope-ΔF508 CFTR at different times after external labeling. BHK-21 cells stably expressing Extope-CFTR and Extope-ΔF508 CFTR were grown at 27° C. in the presence of 2 mM butyrate. Extope-CFTR and the ΔF508 variant were labeled at the cell surface and visualized as described in FIG. 8 at the times indicated. Nuclei were stained with propidium iodide.

FIG. 9C. Chemiluminescence detection of cell surface Extope-CFTR and Extope-ΔF508 CFTR. Extope-CFTR was labeled with anti-HA antibody 16B12 on cells, which had been grown at 27° C. in the presence of butyrate. Cells were then re-incubated at 37° C. for the times indicated. Remaining Extope-CFTR (circles) and Extope-ΔF508 (diamonds) on the cell surface were detected using sheep anti-mouse IgG horseradish peroxidase conjugate and chemiluminescence substrate as described in FIG. 6. Each point represents the average of eight wells and standard deviations are indicated.

FIG. 10A. Incubation at 16° C. blocks endocytosis and allows intracellular detection of ΔF508-CFTR. Cells were grown at 27° C. with 2 mM butyrate and incubated for 45 minutes at 16° C. Then cell surface pools of Extope-CFTR and Extope-ΔF508 CFTR were labeled with 12CA5 mAb for 30 minutes at the same temperature. Subsequently cells were washed and reincubated in regular media for 1 hour. Extope-CFTR was then detected in cells washed with regular PBS pH 7.4 (no acidic wash) or after an acidic wash (acidic wash). Nuclei were stained with propidium iodide.

FIG. 10B. Lysosomal and proteasomal inhibitors inhibit endocytic turn over of ΔF508-CFTR. Cell surface Extope-CFTR or Extope-ΔF508 CFTR were labeled with 16B12 as described in FIG. 2A. Cells were re-incubated at 37° C. for 7 hours with either lysosomal inhibitors pepstatin-A and leupeptin (Pep+Leu, each 50 µg/ml) and E64 (3.5 µg/ml) or proteasomal inhibitors lactacystin (50 µM) and MG132 (50 µM) or without drug (control) and stained for immunofluorescence microscopy. Nuclei were stained with propidium iodide.

FIG. 10C. ΔF508 CFTR accumulates in lysosomes in the presence of the lysosomal inhibitors. Cells were treated with lysosomal inhibitors pepstatin-A and leupeptin as described in FIG. 5B. Extope-ΔF508 CFTR was labeled with 16B12 at the cell surface and detected 7 hours later using goat anti-mouse IgG Alexa Fluor 488 conjugate. Lysosomes were labeled with Lysotracker Red (Molecular Probes).

FIG. 10D. Proteasomal inhibitor increases the amount of CFTR retained at the cellular surface. Extope-CFTR and ΔF508 CFTR were labeled on intact pre-cooled cells on ice for 30 minutes with 16B12 mAb and cells were reincubated in the presence or absence of lactacystin (25 µM) for indicated times. Cell surface Extope-CFTR was detected in a chemiluminescence assay at indicated times using sheep anti-mouse peroxidase conjugate and chemiluminescence. Each experiment was performed with 8 replicates and standard deviations are indicated.

FIG. 11A. Rab5DN stabilized Extope-ΔF508 CFTR at the plasma membrane,

FIG. 11B, Rab11 increased cell surface Extope-ΔF508 CFTR,

FIG. 11C, Rab4 did not significantly change the turn over of Extope-ΔF508 CFTR,

FIG. 11D, Rab7DN overexpression stabilized intracellular pools of Extope-ΔF508CFTR.

FIG. 11E. Images were analyzed with ImageJ 1.30v software to determine the mean fluorescence per cell on overexpression of different Rab GTPases. Each point represents the average of at least 10 cells and standard deviations are indicated.

DETAILED DESCRIPTION OF THE PREFERRED EMBODIMENTS

Figure 1A:
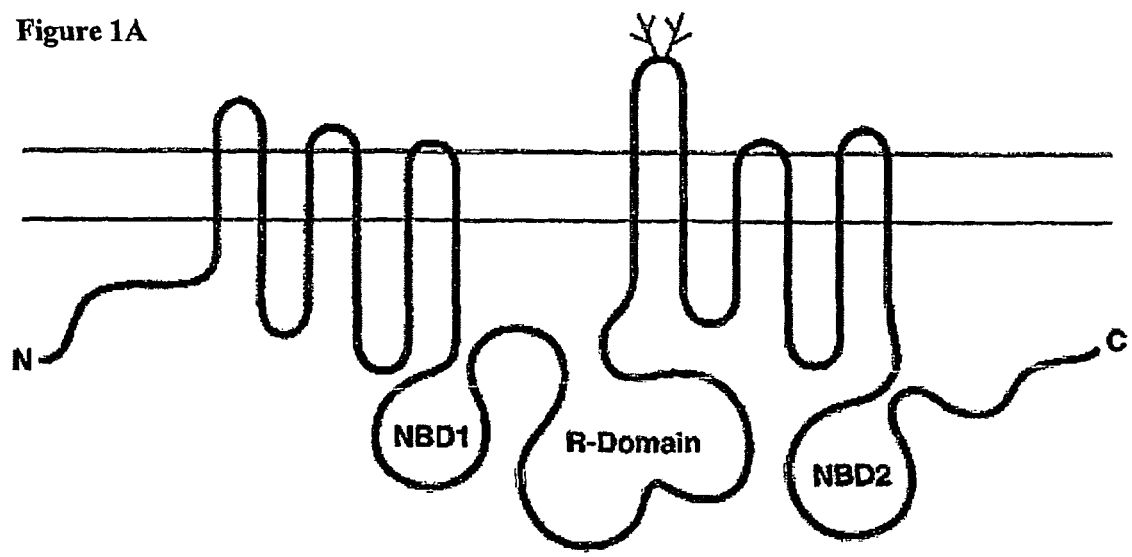
FIG. 1A. 2D topology of CFTR relative to the membrane (horizontal lines).

Amino acid sequences disclosed herein are presented in the amino to carboxy direction, from left to right, unless indicated otherwise. The amino and carboxy groups are not presented in the sequence. Nucleotide sequences are presented herein by single strand only, in the 5' to 3' direction, from left to right, unless indicated otherwise. Nucleotides and amino acids are represented herein in the manner recommended by the IUPAC-IUB Biochemical Nomenclature Commission, or (for amino acids) by standard one letter code or three letter code, in accordance with 37 C.F.R §1.822 and established usage. See, e.g., Patent In User Manual, 99-102 (Nov. 1990) (U.S. Patent and Trademark Office).

All United States patent references cited herein are to be incorporated by reference herein in their entirety.

1. DEFINITIONS

"Cystic fibrosis transmembrane conductance regulator" (or "CFTR") gene or nucleic acid as used herein is known and described in, for example, U.S. Pat. No. 6,201,107 to Lap-Chee Tsui et al. and U.S. Pat. No. 5,776,677 to Lap-Chee Tsui et al., the disclosures of which applicants specifically intend be incorporated by reference herein in their entirety. The CFTR protein is described in, for example, U.S. Pat. No. 5,543,399 to Riordan et al, the disclosure of which is incorporated by reference herein in its entirety. The CFTR nucleic acid and protein is further described in NCBI Number NM 000492 and NCBI Number P13569. CFTR nucleic acids and proteins herein are generally mammalian (e.g., dog, cat, mouse, rat, rabbit) and preferably human. The CFTR protein has six extracytoplasmic loops designated EL1 through EL6. CFTR as used herein may be wild-type (e.g., contains phenylalanine at position 508) or a mutated CFTR that would produce disease in a subject containing such a mutation (e.g., a deletion of phenylalanine at position 508 or other mutation as discussed below).

"Detectable epitope" as used herein may be any segment of nucleic acid encoding a polypeptide that serves as one member of a specific binding pair and which polypeptide can be detected by another corresponding member of a specific binding pair (such as an antibody) in any type of binding assay. The influenza hemagluttinin (HA) epitope may be used, or any other suitable epitope including but not limited to HSV: QPELAPEDPED (SEQ ID NO: 1); T7 Tag: MASMTG-GQQMG (SEQ ID NO: 2); Flag: DYKDDDDK (SEQ ID NO: 3); Xpress: DLYDDDDK (SEQ ID NO: 4); V5: GKPIP-NPLLGLDST (SEQ ID NO: 5); c-myc: EQKLISEEDL (SEQ ID NO: 6) or other specific epitope not normally detected on the surface of cells and for which a monoclonal antibody of sufficiently high sensitivity and selectivity is available. An example of the latter is the mouse monoclonal antibody 42.4 recognizing an epitope between amino acids 723 and 732 of human MRP1 (multidrug resistance protein 1; Hou et al, 2000). In general such epitopes are from 3, 4, 5 or 7 amino acids in length up to 15 amino acids in length, or more.

"Flanking polypeptide" as used herein refers to a polypeptide spliced (typically directly spliced or directly contiguous with) in the N-terminal or C-terminal direction to the detectable epitope.

As used herein, the term "antibody" refers to intact molecules as well as fragments thereof, such as Fab, F(ab')2, etc. which are capable of binding the epitopic determinant. Antibodies may be of any type of immunoglobulin, including but not limited to IgG and IgM, and may be monoclonal or polyclonal. Antibodies that bind epitopes can be prepared using intact polypeptides or fragments containing small peptides of interest as the immunizing antigen.

"Epitope" as used herein, refers to that fragment of a molecule (e.g., a polypeptide) that makes contact with a particular antibody.

A "deletion", as used herein, refers to a change in the amino acid or nucleotide sequence and results in the absence of one or more amino acid residues or nucleotides.

An "insertion" or "addition", as used herein, refers to a change in an amino acid or nucleotide sequence resulting in the addition of one or more amino acid residues or nucleotides, respectively, as compared to the naturally occurring molecule.

A "substitution", as used herein, refers to the replacement of one or more amino acids or nucleotides by different amino acids or nucleotides, respectively.

2. RECOMBINANT NUCLEIC ACIDS, VECTORS AND CELLS

The production of cloned genes, recombinant DNA, vectors, transformed host cells, proteins and protein fragments by genetic engineering is well known. See, e.g., U.S. Pat. No. 4,761,371 to Bell et al. at Col. 6 line 3 to Col. 9 line 65; U.S. Pat. No. 4,877,729 to Clark et al. at Col. 4 line 38 to Col. 7 line 6; U.S. Pat. No. 4,912,038 to Schilling at Col. 3 line 26 to Col. 14 line 12; and U.S. Pat. No. 4,879,224 to Wallner at Col. 6 line 8 to Col. 8 line 59.

As noted above, the present invention provides a recombinant nucleic acid encoding a modified cystic fibrosis transmembrane conductance regulator (CFTR) protein. The nucleic acid is modified by the insertion of a first heterologous segment encoding a detectable epitope in a region encoding an extracytoplasmic loop, such as at least one of the first, second, third, fourth, fifth or sixth extracytoplasmic loops (EL1, EL2, EL3, EL4, EL5 or EL6). An insertion of a detectable epitope within the region encoding EL2 is currently preferred (e.g., between amino acids W216 and Q220 of the CFTR protein, or the corresponding coding region of the CTFR nucleic acid).

The detectable epitope, along with its flanking sequences are preferably inserted into the extracytoplasmic loop without deletion of corresponding or native segments of the extracytoplasmic loop.

The nucleic acid may be "wild-type", that is, encoding phenylalanine at position 508 of the encoded CFTR protein, or the nucleic acid may be mutated as found in patients afflicted with cystic fibrosis, such as a nucleic acid encoding a deletion of phenylalanine at position 508 of the encoded CFTR protein. The nucleic acid may contain other such mutations, as there are over 1,000 mutations known that cause cystic fibrosis in patients, many of which disrupt protein folding or maturation, and which mutations can be included in a CFTR nucleic acid or protein used to carry out the present invention to determine the effect of compounds in facilitating the folding or maturation of the CFTR protein.

The recombinant nucleic acid may be further modified to incorporate a second heterologous segment encoding a flanking polypeptide positioned 5' (N-terminal) to the first heterologous segment; and a third heterologous segment encoding a flanking polypeptide positioned 3' (C-terminal) to the first heterologous segment. Such flanking polypeptides are typically at least 10, 12 or 14 amino acids in length, up to about 30, 40 or 50 amino acids in length, or more. The flanking polypeptides may be naturally occurring polypeptides or synthetic polypeptides, but the amino acid content thereof should preferably be selected so that the flanking polypeptides are hydrophilic rather than lipophilic (when considered together along with the detectable epitope) so that they are expressed as an extracytoplasmic loop in the CFTR protein. In one embodiment, the flanking segments are derived from EL1 (G103 to R117) and EL4 (L881 to S911), portions of which segments may optionally be spliced together to produce each heterologous flanking segment. Note that the flanking segments and epitope need not be inserted as discrete and separate units, but may be assembled in any manner that is convenient (e.g., by synthesis and insertion of a single polynucleotide that encodes flanking segments and epitope).

A vector is a replicable DNA construct. Vectors are used herein either to amplify DNA encoding the proteins of the present invention or to express the proteins of the present invention. An expression vector is a replicable DNA construct in which a DNA sequence encoding the proteins of the present invention is operably linked to suitable control sequences capable of effecting the expression of proteins of the present invention in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

Vectors comprise plasmids, viruses (e.g., adenovirus, cytomegalovirus), phage, retroviruses and integratable DNA fragments (i.e., fragments integratable into the host genome by recombination). The vector replicates and functions independently of the host genome, or may, in some instances, integrate into the genome itself. Expression vectors should contain a promoter and RNA binding sites which are operably linked to the gene to be expressed and are operable in the host organism.

DNA regions are operably linked or operably associated when they are functionally related to each other. For example, a promoter is operably linked to a coding sequence if it controls the transcription of the sequence; a ribosome binding site is operably linked to a coding sequence if it is positioned so as to permit translation. Generally, operably linked means contiguous and, in the case of leader sequences, contiguous and in reading phase.

Host cells are cells that have been transformed or transfected with vectors containing DNA coding for proteins of the present invention. Such cells express the protein when used to carry out the assays described below, but such cells need not express protein if used to simply propagate or reproduce the recombinant nucleic acid.

Suitable host cells include prokaryotes, yeast cells, prokaryotic or higher eukaryotic organism cells. Prokaryote host cells include gram negative or gram positive organisms, for example *Escherichia coli* (*E. coli*) or *Bacilli*. Higher eukaryotic cells include established cell lines of mammalian origin as described below.

Cultures of cells derived from multicellular organisms are a desirable host for carrying out the present invention. In principal, any higher eukaryotic cell culture is workable, whether from vertebrate or invertebrate culture, including insect cells. Propagation of such cells in cell culture has become a routine procedure. See Tissue Culture, Academic Press, Kruse and Patterson, editors (1973). Examples of useful host cell lines are VERO and HeLa cells, Chinese hamster ovary (CHO) cell lines, and WI138, BHK, COS-7, CV, and MDCK cell lines. Expression vectors for such cells ordinarily include (if necessary) an origin of replication, a promoter located upstream from the gene to be expressed, along with a ribosome binding site, RNA splice site (if intron-containing genomic DNA is used), a polyadenylation site, and a transcriptional termination sequence.

The transcriptional and translational control sequences in expression vectors to be used in transforming vertebrate cells are often provided by viral sources. For example, commonly used promoters are derived from polyoma, Adenovirus 2, and Simian Virus 40 (SV40). See, e.g., U.S. Pat. No. 4,599,308. The early and late promoters are useful because both are obtained easily from the virus as a fragment which also contains the SV40 viral origin of replication. See Fiers et al., Nature 273, 113 (1978). Further, the protein promoter, control and/or signal sequences, may also be used, provided such control sequences are compatible with the host cell chosen.

An origin of replication may be provided either by construction of the vector to include an exogenous origin, such as may be derived from SV40 or other viral source (e.g. Polyoma, Adenovirus, VSV, or BPV), or may be provided by the host cell chromosomal replication mechanism. If the vector is integrated into the host cell chromosome, the latter may be sufficient.

3. SCREENING METHODS

The present invention provides a method of screening compounds for activity in promoting, facilitating, increasing or enhancing the transport of the cystic fibrosis transmembrane conductance regulator protein to the cell surface. In general, the method comprises:

(a) providing a cell that contains and expresses a recombinant nucleic acid encoding a modified CFTR protein as described herein (e.g., wherein the nucleic acid is modified by the insertion of a first heterologous segment encoding a detectable epitope in the region encoding the first, second, third, fourth, fifth or sixth extracytoplasmic loops);

(b) administering a test compound to the cell; and then (c) detecting the presence or absence of increased amounts of the detectable epitope on the extracellular membrane surface of the cell, the presence of increased amounts of the detectable epitope on the extracellular membrane surface of the cell indicating the compound promotes the transport of the CFTR to the cell surface. "Increased amounts" may be any increased level of the CFTR, including increased peak amounts, increased total amount, increased amounts over time (as may be achieved by a compound that decreases the turnover and hence increases the lifespan of CFTR once it has located to the cell surface, even if the total amount of CFTR transported to the cell surface remains the same), or any combination thereof.

Test compounds, including combinatorial libraries of such compounds, that may be screened for activity by the methods of the invention are, in general, small organic compounds (i.e., non-oligomers), oligomers, or combinations thereof. Compounds which exhibit activity in these methods are referred to as "active compounds" below.

Small organic compounds (or "non-oligomers") include a wide variety of organic molecules, such as heterocyclics, aromatics, alicyclics, aliphatics and combinations thereof, comprising steroids, antibiotics, enzyme inhibitors, ligands, hormones, drugs, alkoids, opioids, terpenes, porphyrins, toxins, catalysts, as well as combinations thereof. Libraries of such compounds are available, examples including benzodiazepine libraries as described in U.S. Pat. No. 5,288,514; pbosphonate ester libraries as described in U.S. Pat. No. 5,420,328, pyrrolidine libraries as described in U.S. Pat. Nos. 5,525,735 and 5,525,734, and diketopiperazine and diketomorpholine libraries as described in U.S. Pat. No. 5,817,751.

Oligomers include oligopeptides, oligonucleotides, oligosaccharides, polylipids, polyesters, polyamides, polyurethanes, polyureas, polyethers, and poly (phosphorus derivatives), e.g. phosphates, phosphonates, phosphoramides, phosphonamides, phosphites, phosphinamides, etc., poly (sulfur derivatives) e.g., sulfones, sulfonates, sulfites, sulfonamides, sulfenamides, etc., where for the phosphorous and sulfur derivatives the indicated heteroatom for the most part will be bonded to C, H, N, O or S, and combinations thereof. Such oligomers may be obtained from combinatorial libraries in accordance with known techniques.

The administering step may be carried out by any suitable technique. In general the administering step is carried out in vitro and hence assays of the present invention are in general in vitro assays. Such assays may be carried out in accordance with known techniques, such as by growing cells in a microtiter plate well or on another suitable carrier, and contacting an aqueous solution containing the compound to be delivered to the cells.

The detecting step may be carried out by immunoassay, including but not limited to radioimmunoassay, enzyme immunoassay, fluorescent or luminescent immunoassay. Such assays are known and may be carried out in accordance with known techniques, including but not limited to those described in U.S. Pat. Nos. 6,551,782; 6,538,113; 6,534,634; 6,531,578; 6,514,770; 4,376,110 and 4,879,219. The detecting step may be a qualitative or quantitative detecting step, and may involve comparing the amount of detectable epitope found on the surface of cells expressing the recombinant nucleic acid with control cells (e.g., the same cells not administered the test compound; cells containing a nucleic acid encoding a mutated modified protein as opposed to a mutated wild-type protein; cells containing no heterologous nucleic acid) or cells receiving various dosages of the test compound, all in accordance with known techniques.

Compounds that promote, increase, facilitate or enhance the transport of the cystic fibrosis transmembrane conductance regulator protein to the cell surface of cells expressing the same, or decrease the turnover of the protein once it has located to the cell surface, can be identified by the processes described above, screened further in vitro or in vivo for activity in treating cystic fibrosis, and/or prepared in a pharmaceutically acceptable carrier in accordance with known techniques and administered to patients in a treatment effective amount (e.g., by parenteral injection, oral administration or inhalation to the lungs) to treat the cystic fibrosis in accordance with known techniques.

The present invention is explained in greater detail in the following non-limiting examples.

Experimental

These examples illustrate the development of a method of detecting the appearance of mutant CFTR from the cell exterior, and its application in a high throughput mode to screen for agents promoting this appearance. The basis of this method was to modify extracytoplasmic loops so that an inserted epitope would be exposed. The rationale was to employ sequences from the two largest loops (EL1 and EL4) presumably most exposed on the extracytoplasmic surface to surround an epitope inserted into another EL. To do this, portions of EL1 and EL4 were spliced into either EL2 or EL6 and then an epitope of an influenza hemagglutinin (HA) was introduced. This was done in a fashion whereby sequences from EL4 interrupted those from EL1 while the epitope sequence interrupted the EL4 sequence; this served to reduce the possibility of homologous recombination between the repeated sequences from EL1 and EL4 when they appeared in EL2 as well as in their native locations.

The methods of generating expressible cDNA constructs coding for these modified CFTRs are shown in FIG. 1, which details the insertion of HA epitope into EL2 and EL6 as performed by polymerase chain reaction (PCR) as diagramed therein. The oligonucleotide primers used are: F-EL2, 5' A$^{637}$GC CGT GTT CTA GAT AAA ATA AGT A$^{661}$ (SEQ ID NO: 7); R-EL2(S422A/3'), 5' G$^{1410}$TC ATC ACC ATT AGC AGT TTT TCT ATT GTT$^{1381}$ (SEQ ID NO: 8); EL2-RI1, 5' ATC CGG GTC ATA GGA AGT ATT/TAA CAA CTC CCA GAT TAG CCC (SEQ ID NO: 9); RI2, 5' GTA TGG ATA AGT ATT CCC TTT GTT/ATC CGG GTC ATA GGA AGT (SEQ ID NO: 10); RI3, 5' GTT AGC GTA GTC AGG AAC GTC GTA/TGG ATA AGT ATT CCC TTT (SEQ ID NO: 11); EL2-FI1, 5' TCG AAG GAG GAA CGC AGT/TTA CAG GCG TCT GCC TTC (SEQ ID NO: 12); FI2, 5' TAC GCT GTC ATC ATT ACA/TCG AAG GAG GAA CGC AGT (SEQ ID NO: 13); FI3, 5' GAC GTT CCT GAC TAC GCT AAC TCT/TAC GCT GTC ATC ATT ACA (SEQ ID NO: 14); EL6-RI1, 5' ATC CGG GTC ATA GGA AGT ATT/TTC TCC TTC TCC TGT TGT (SEQ ID NO: 15); EL6-FI1, 5' ACA TCG AAG GAG GAA CGC AGT/GGA AGA GTT GGT ATT ATC (SEQ ID NO: 16); F-EL6, 5' G$^{2899}$CC GAC ACT TTG CTT GCT ATG G$^{2920}$ (SEQ ID NO: 17) and R-EL6 (K1250Q/3'), 5' T$^{3897}$GA TAA CAA AGT ACT CTG CCC TGA TCC AGT TCT$^{3865}$ (SEQ ID NO: 18).

Figure 1B:
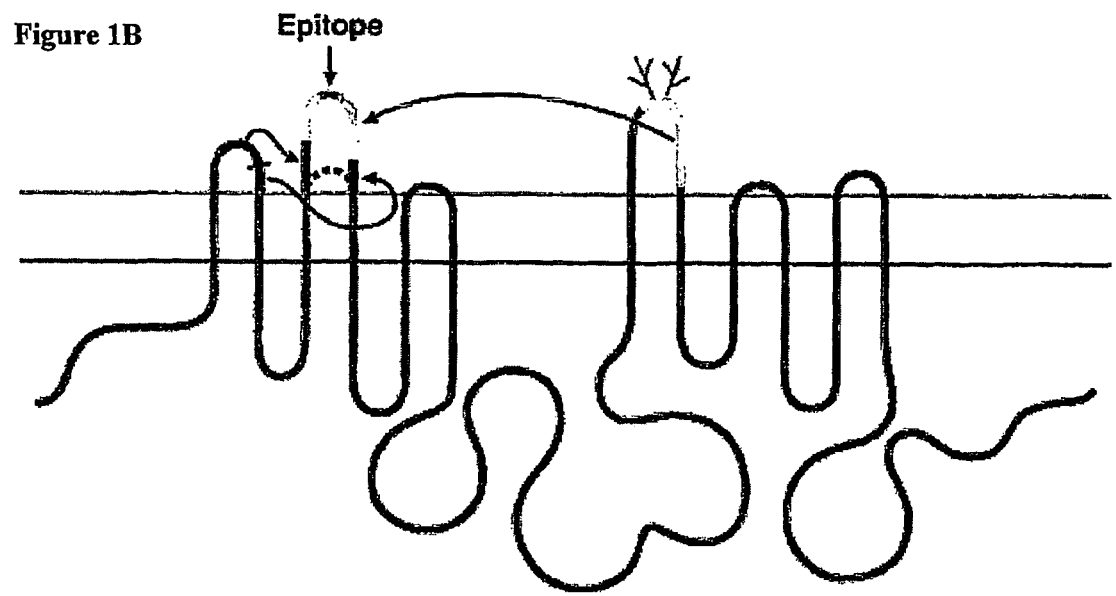
FIG. 1B. Indication of the portions of EL1 and EL4 introduced into EL2 to insure exposure of the epitope. EL6 rather than EL2 was similarly altered (not shown).
Figure 1D:
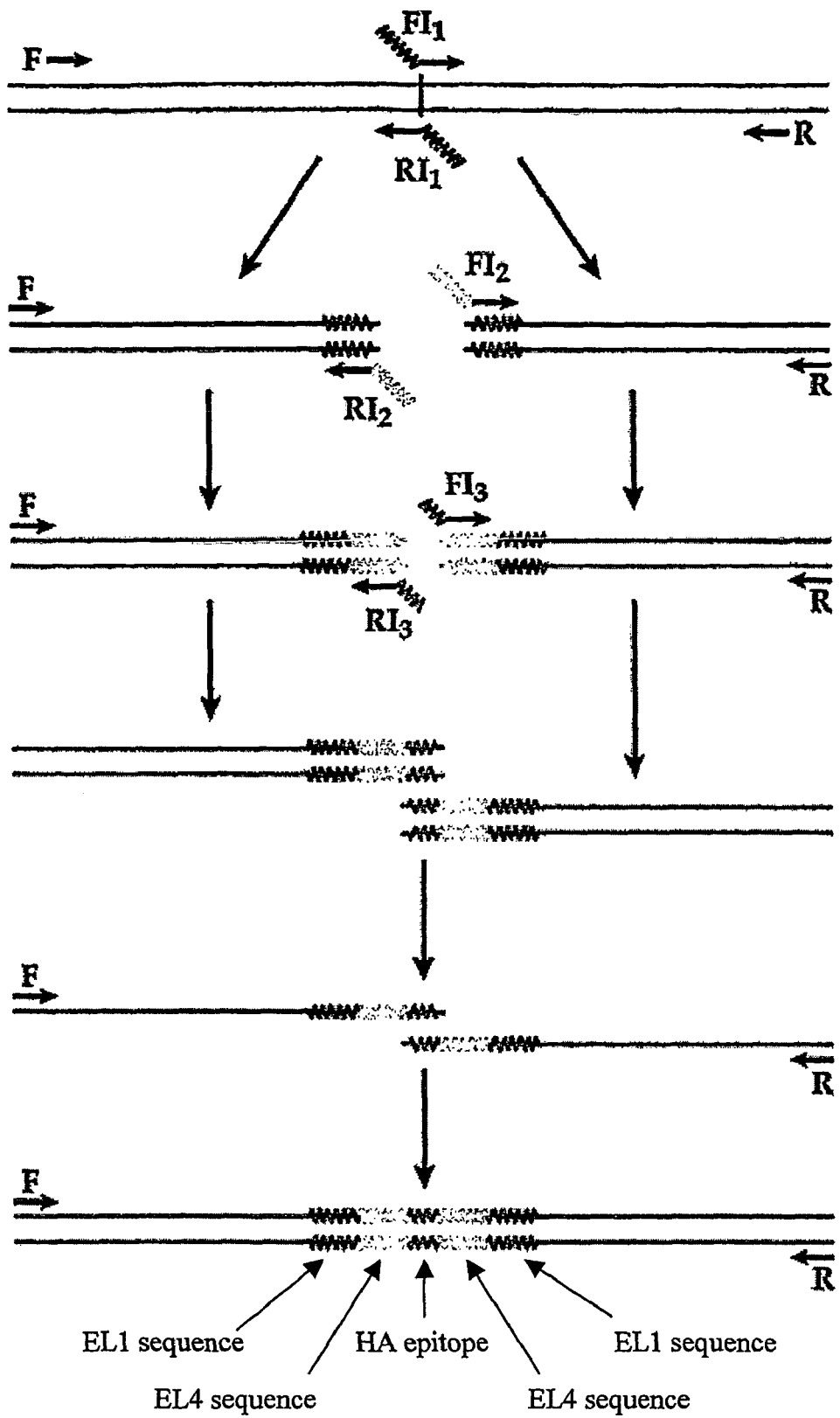
FIG. 1D. PCR based in vitro mutagenesis to generate cDNAs coding for modified EL2 or EL6.

FIG. 1A details the 2D topology of CFTR relative to the membrane (horizontal lines). The N- and C-termini, the cytoplasmic nucleotide-binding domains (NBD1 and NBD2) and R-domain are indicated as are the oligosaccharide chains (branched twigs) on the fourth extracytoplasmic loop (EL4). FIG. 1B indicates the portions of EL1 and EL4 introduced into EL2 to insure exposure of the epitope. EL6 rather than EL2 was similarly altered (not shown). FIG. 1C illustrates amino acid sequence changes involved in modification of extracytoplasmic loops EL2 or EL6 to provide exposed epitope tag (Extope-CFTR). FIG. 1D illustrates PCR based in vitro mutagenesis to generate cDNAs coding for modified EL2 or EL6, as follows:

EL1:    GRIIASYDPDNKEER                             (SEQ ID NO:19)

EL2:    WELLQ                                        (SEQ ID NO:20)

EL4:    LWLLGNTPLQDKGNSTHSRNNSYAVIITSTS              (SEQ ID NO:21)

EL6:    EGEGR                                        (SEQ ID NO:22)

Final Modification:

EL2:    WEL*NTS*YDPDNKGNTYPYDVPDYANSYAYIITS*KEERS*LQ   (SEQ ID NO:23)

EL6:    EGE*NTS*YDPDNKGNTYPYDVPDYANSYAYIITS*KEERS*GR   (SEQ ID NO:24)

SYDPDN (SEQ ID NO: 27) AND KEER (SEQ ID NO: 28) COME FROM EL 1 (underlined in FIG. 1C); NT IS RANDOMLY INSERTED SEQUENCE; KGNT (SEQ ID NO: 29) AND NSYAYIITS (SEQ ID NO: 30) COME FROM EL4 (in italics in FIG. 1C); AND YPYDVPDYA (SEQ ID NO: 31) IS THE HA TAG (highlighted in bold in FIG. 1C).

Primers for EL2 insertion (PCR fragment covers XbaI (649) and HhaI (1172) sites for cloning):

primer 130:
5' A$^{637}$GCCGTGTTCTAGATAAAATAAGTA$^{661}$          (SEQ ID NO:7)

S422A/3':
5' G$^{1410}$TCATCACCATTAGCAGTTTTTCTATTGTT$^{1381}$   (SEQ ID NO:8)

Primers for EL6 insertion (PCR fragment covers DraIII site (3328) and BbrPI (3723) sites for cloning):

Primer 746:
5' G$^{2899}$CCGACACTTTGCTTGCTATGG$^{2920}$                          (SEQ ID NO:17)

Primer K1250Q/3':
5' T$^{3897}$GATAACAAAGTACTCTGCCCTGATCCAGTTCT$^{3865}$              (SEQ ID NO:18)

PCR for EL2:
GLIWEL/NTSYDPD                                                      (SEQ ID NO:32)
       TSYDPD/NKGNTYPY                                              (SEQ ID NO:33)
              GNTYPY/DVPDYANS                                       (SEQ ID NO:34)
                     DVPDYANS/YAYIIT                                (SEQ ID NO:35)
                              YAYIIT/SKEERS                         (SEQ ID NO:36)
                                     SKEERS/LQASAF                  (SEQ ID NO:37)

PCR for EL6:
TTGEGE/NTSYDPD                                                      (SEQ ID NO:38)
       TSYDPD/NKGNTYP                                               (SEQ ID NO:39)
              KGNTYP/YDVPDYAN                                       (SEQ ID NO:40)
                     YDVPDYAN/SYAYII                                (SEQ ID NO:41)
                              NSYAYII/TSKEER                        (SEQ ID NO:42)
                                      TSKEERS/GRVGII                (SEQ ID NO:43)

Oligo for GLIWEL/NTSYDPD:
Forward:
5' GGGCTAATCTGGGAGTTGTTA/AATACTTCCTATGACCCGGAT                      (SEQ ID NO:44)

Reverse: EL2-RI1
5' ATCCGGGTCATAGGAAGTATT/TAACAACTCCCAGATTAGCCC                      (SEQ ID NO:9)

Oligo for TSYDPD/NKGNTYPY:
Forward:
5' ACTTCCTATGACCCGGAT/AACAAAGGGAATACTTATCCATAC                       (SEQ ID NO:45)

-continued

```
Reverse: RI2
5' GTATGGATAAGTATTCCCTTTGTT/ATCCGGGTCATAGGAAGT      (SEQ ID NO:10)

Oligo for KGNTYP/YDVPDYAN:
Forward:
5' AAAGGGAATACTTATCCA/TACGACGTTCCTGACTACGCTAAC     (SEQ ID NO:46)

Reverse: RI3
5' GTTAGCGTAGTCAGGAACGTCGTA/TGGATAAGTATTCCCTTT     (SEQ ID NO:11)

Oligo for DVPDYANS/YAYIIT: FI3:
5' GACGTTCCTGACTACGCTAACTCT/TACGCTGTCATCATTACA     (SEQ ID NO:14)

Oligo for YAYIIT/SKEERS: FI2:
5' TACGCTGTCATCATTACA/TCGAAGGAGGAACGCAGT           (SEQ ID NO:13)

Oligo for SKEERS/LQASAF: FI1:
5' TCGAAGGAGGAACGCAGT/TTACAGGCGTCTGCCTTC           (SEQ ID NO:12)

Oligo for TTGEGE/NTSYDPD:
Forward:
5' ACAACAGGAGAGGAGAA/AATACTTCCTATGACCCGGAT         (SEQ ID NO:47)

Reverse: RI1:
5' ATCCGGGTCATAGGAAGTATT/TTCTCCTTCTCCTGTTGT        (SEQ ID NO:15)

Oligo for TSKEERS/GRVGII:
Forward: FI1:
5' ACATCGAAGGAGGACGCAGT/GGAAGAGTTGGTATTATC         (SEQ ID NO:16)
```

The PCR fragments were cloned into pBluescript and sequenced completely. The counterpart fragment in pNUT/CFTR (Chang et al, 1993) was replaced by XbaI (649)-HhaI (1172) containing HA epitope insertion in EL2 to generate pNUT/EL2HA/CFTR. The counterpart fragment in pNUT/CFTR was replaced by DraIII (3328)-BbrPI (3723) containing HA epitope insertion in EL6 to generate pNUT/EL6HA/CFTR.

Figure 2:
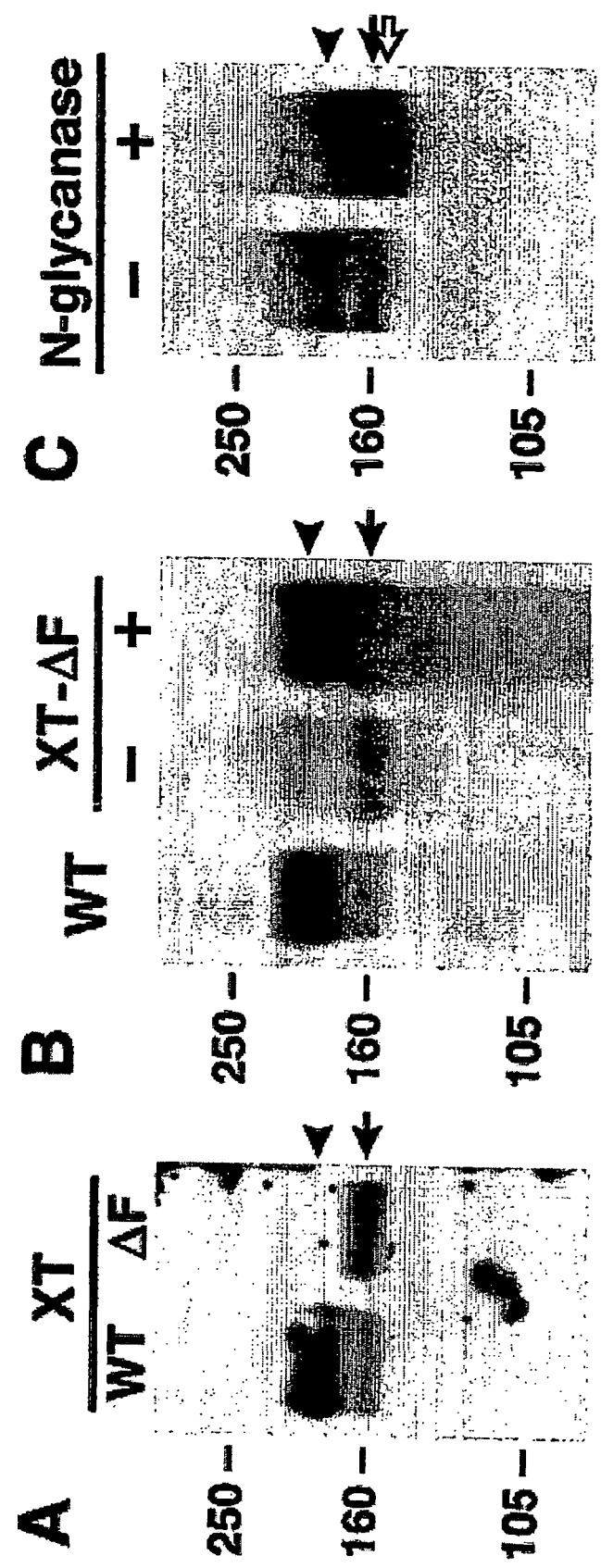
FIG. 2. Western blot detection of wild-type and ΔF508 CFTR with modification of EL2.
Figure 3:
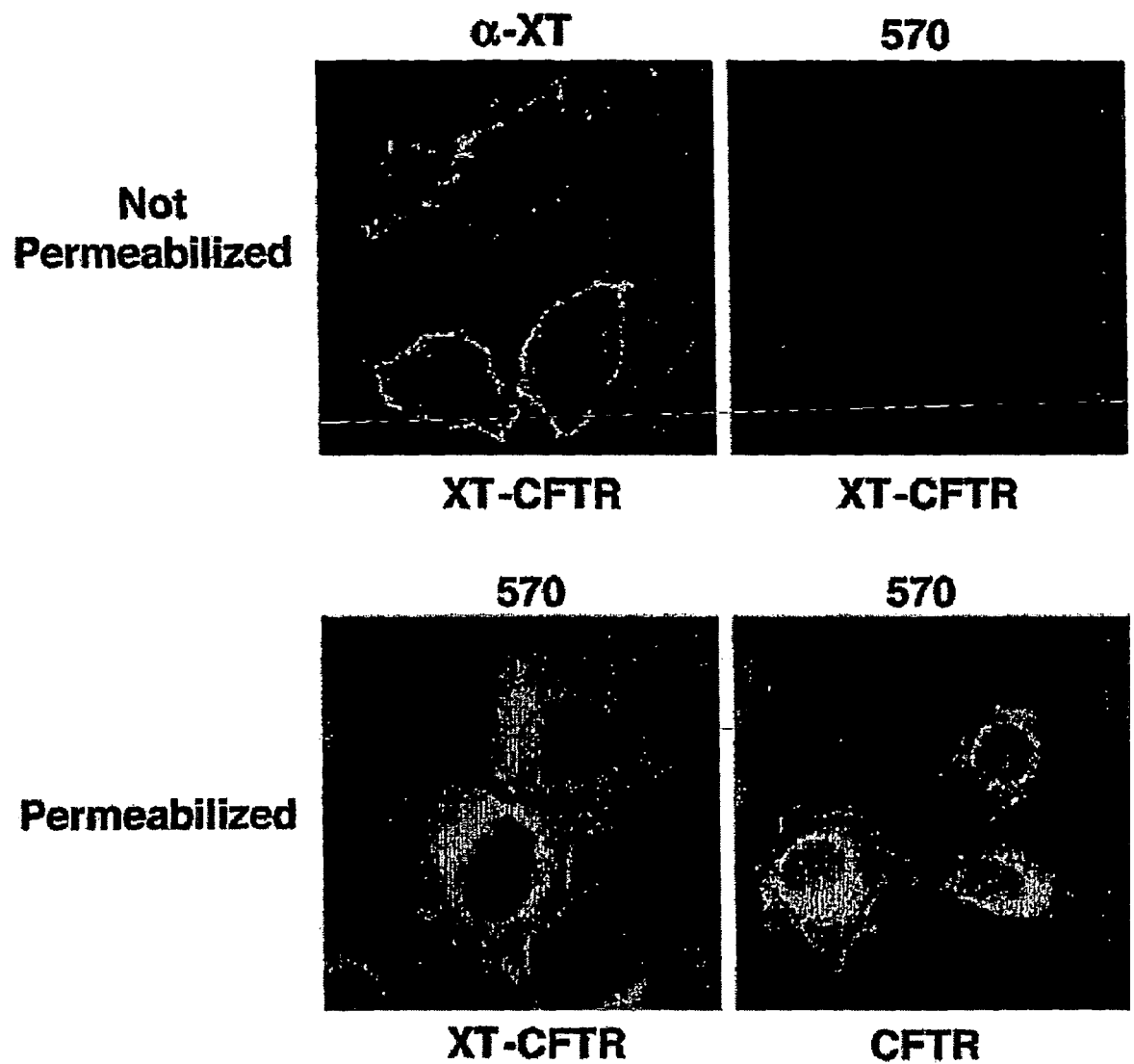
FIG. 3. Immunofluorescence microscopy of BHK-21 cells expressing wild-type CFTR with or without modification of EL2. In the upper two panels surface CFTR is readily detected with an antibody to the EL2 epitope (α-XT; left panel) but not by an antibody to a cytoplasmic epitope in the R-domain of CFTR (570; right panel). Lower panels show that CFTR is detected by both antibodies when cells are permeabilized by treatment with 0.1% saponin.
Figure 4:
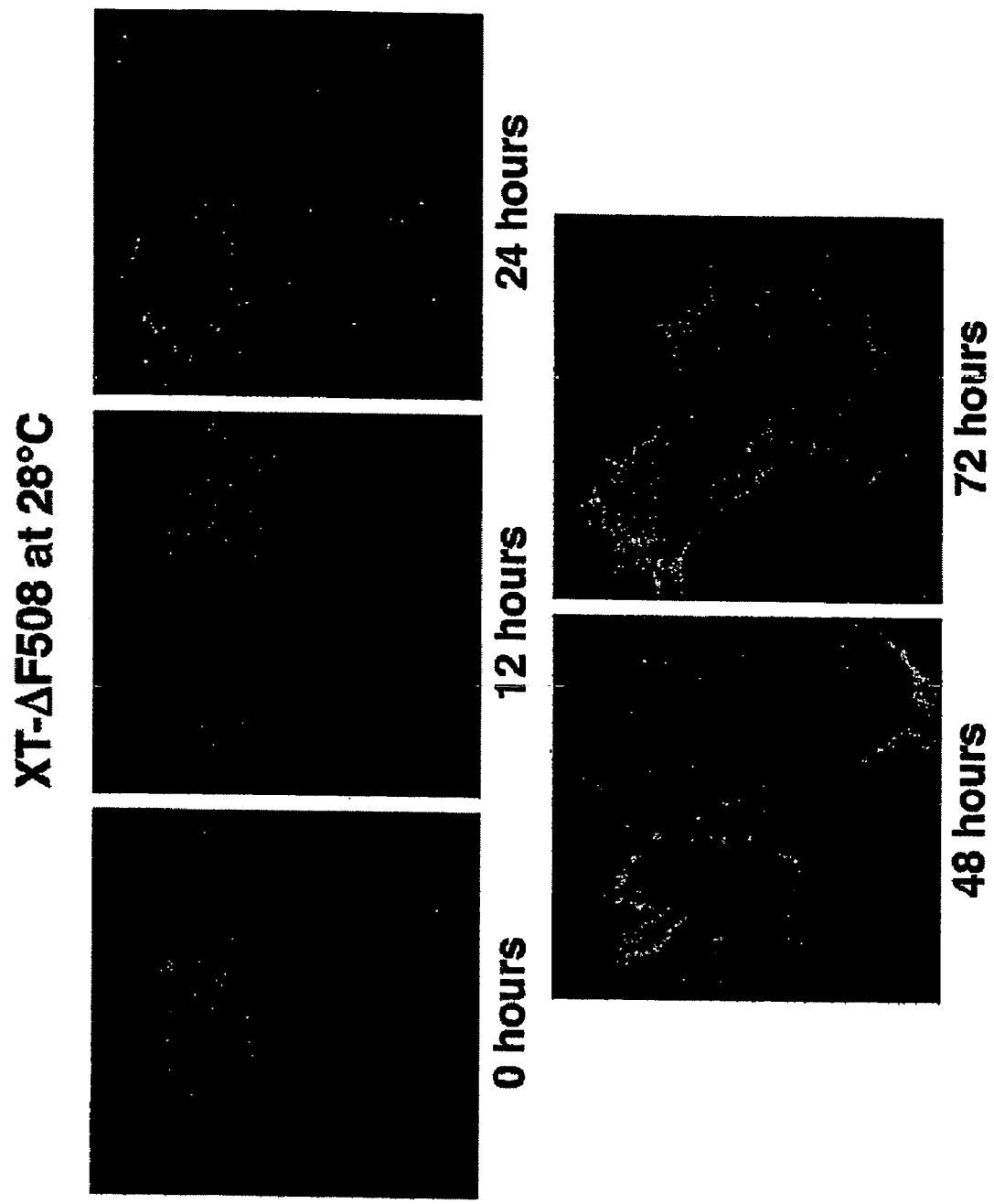
FIG. 4. Immunofluorescence microscopy showing detection of ΔF508 CFTR with modified EL2 at the surface of cells grown at 28° C. for varying time periods. Readily detectible amounts of XT-ΔF508 CFTR appear by 24 h with progressively stronger signals at 48 and 72 h.

Verification of utility. BHK-21 cells stably expressing either the EL2 or EL6 modified wild-type and ΔF508 CFTR cDNA constructs described above were established and the expression of these modified CFTRs assessed. FIG. 2 shows Western blots indicating expression of the EL2 constructs. These EL2 modified variants appeared most similar to unmodified wild-type and mutant CFTR with almost the same ratio of mature to immature forms, the only difference being the increased apparent molecular size due to the insertions into EL2. In contrast the EL6 modified variants exhibits a much lower ratio of mature to immature forms. This illustrates the difficulty in modifying CFTR to make it detectable without compromising its biosynthetic maturation as so many mutations either created in vitro or occurring in patients are known to do (Seibert et al., 1997). Since the EL2 modified variants appeared to behave as unmodified wild-type and ΔF508 CFTR they were characterized further. FIG. 3 shows that the wild-type version (XT-CFTR) was prominently displayed on the surface of unpermeabilized cells when detected with an antibody recognizing the epitope in EL2 but was undetectable with an antibody recognizing a cytoplasmic epitope in the native CFTR sequence. However when the cells were permeabilized CFTR was equally detectible by either antibody. The ΔF508 variant with EL2 modified (XT-ΔF508) was undetectable in cells grown at 37° C. (FIG. 4, first panel). However when these cells were grown at 28° C. for increasing lengths of time, which is known to promote ΔF508 maturation, the XT-ΔF508 became detectible at the cell exterior (FIG. 4).

Figure 5:
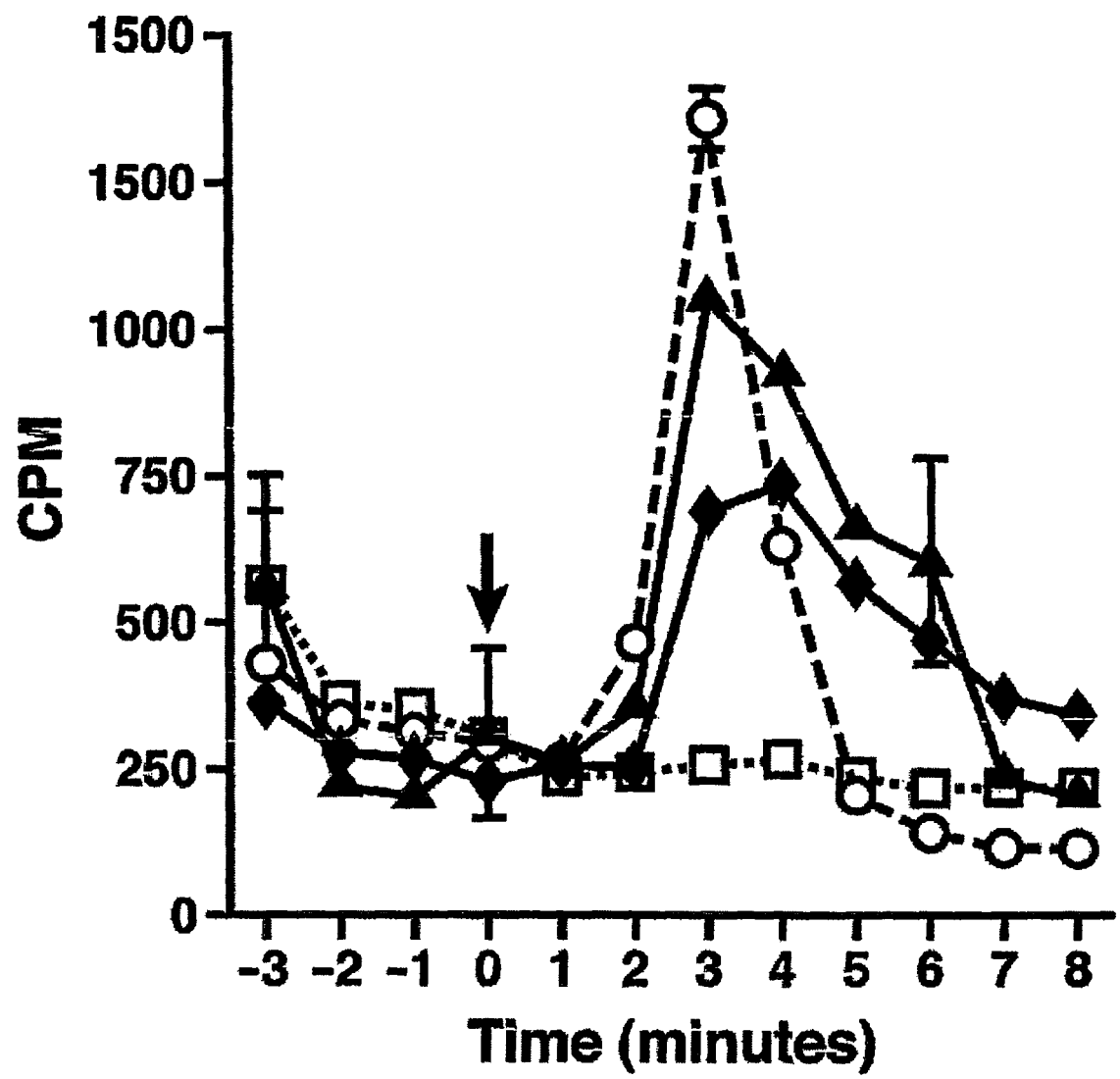
FIG. 5. CFTR chloride channel activity as monitored by $^{36}Cl$ efflux from cells expressing wild-type CFTR (○), ΔF508 CFTR without (◆) or with (▲) 2 mM sodium butyrate or no CFTR (□). Cells were preloaded with $^{36}Cl$ and then exposed to forskolin (10 μM) and IBMX (1 mM) at time 0. The amounts of $^{36}Cl$ radioactivity released from the cells in subsequent 1 min intervals was monitored by scintillation counting. Efflux from ΔF508 CFTR expressing cells grown at 28° C. in the presence of butyrate for 48 h was nearly as great as from cells expressing wild-type CFTR. These results show that both wild-type and ΔF508 CFTR retain chloride channel activity after the modification of EL2.

To determine the functional capability of the EL2 modified variants, rates of cyclic AMP stimulated $^{36}Cl$ efflux from cells expressing them were measured. The rate of efflux from cells expressing wild-type XT-CFTR was similar to that with unmodified wild-type (FIG. 5). With XT-ΔF508 expressing cells grown at 28° C. rates were roughly half that of wild-type but when transcription and therefore the amount of expression was stimulated by butyrate the rates more closely approaches those of wild-type. These observations demonstrate that the XT-ΔF508 protein when allowed to mature in cells grown at reduced temperature is capable of regulated chloride channel activity just as is the unmodified ΔF508 protein under these conditions.

Figure 6:
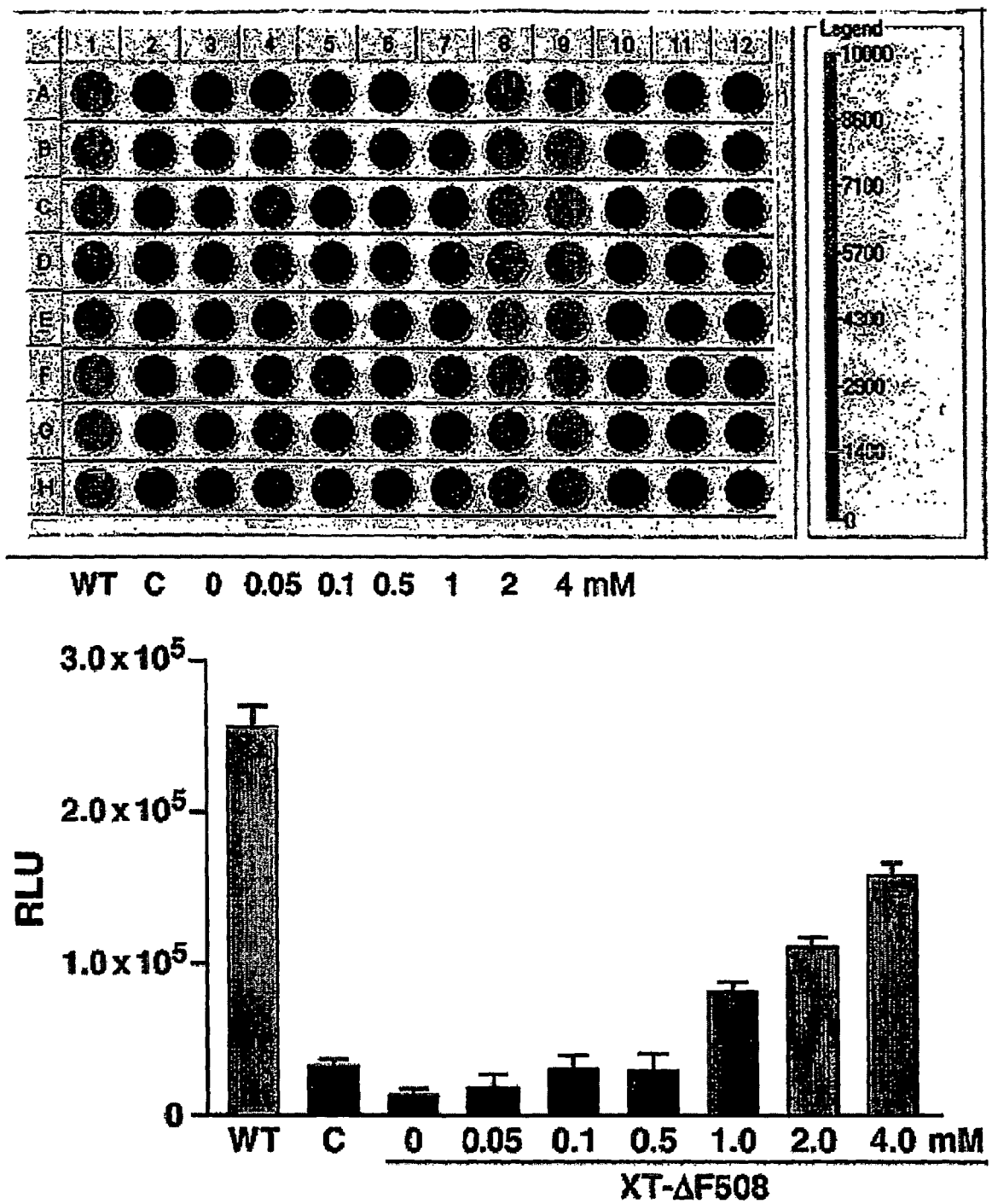
FIG. 6. Quantitative detection of CFTR with EL2 epitope (XT-CFTR) at surface of cells grown in 96 well microtiter plates. Cells were washed, fixed and exposed to an antibody recognizing the external epitope, washed again and incubated with a horseradish peroxidase coupled second antibody and then with a peroxidase substrate that becomes luminescent after peroxidation. Luminescent signals in each well were quantitated in either a Packard Microplate Luminescence Counter or a Perkin Elmer VICTOR$^2$ Multilabel Counter. Increasing amounts of ΔF508 CFTR with modified EL2 is detected at the surface of cells grown at 28° C. for 24 h in the presence of increasing concentrations of sodium butyrate. The upper panel shows a color-coded qualitative read out from a Perkin Elmer VICTOR$^2$ Multilabel counter with blue (dark) to red (light) indicating low to high intensity. The corresponding quantitative signals are shown below. This illustrates that the influence of conditions causing appearance of increasing amounts of ΔF508 at the cell surface are readily detected by the assay.

To provide a more facile and quantifiable means of detecting EL2 modified CFTR on the cell surface, cells were plated on 96-well microtiter plates. The amount of surface epitope was measured either by luminometry or time resolved fluorescence. An experiment illustrating the first is shown in FIG. 6. After incubation with a primary unlabeled mouse antibody to the epitope (HA11, Babco) and washing, a secondary horseradish peroxidase coupled antibody recognizing mouse IgG was added followed by peroxidase substrate that luminesces when peroxidized. Luminescence was measured in each well in one of two different luminescence plate readers. A strong signal is obtained in the replicate row of wild-type XT-CFTR expressing cells and signals of strengthening intensity are obtained in rows of XT-ΔF508 cells grown at 28° C. with increasing concentrations of butyrate. With the maximal butyrate dose the XT-ΔF508 signal is more than half that of the wild-type.

This assay is suitable for the screening of large numbers of compounds for their ability to influence the appearance of ΔF508 CFIR at the cell surface. This in turn may yield a potential drug, drug scaffold or lead compound for the treatment of CF patients with a ΔF508 or other mutation preventing conformational maturation and transport to the cell surface.

Figure 7:
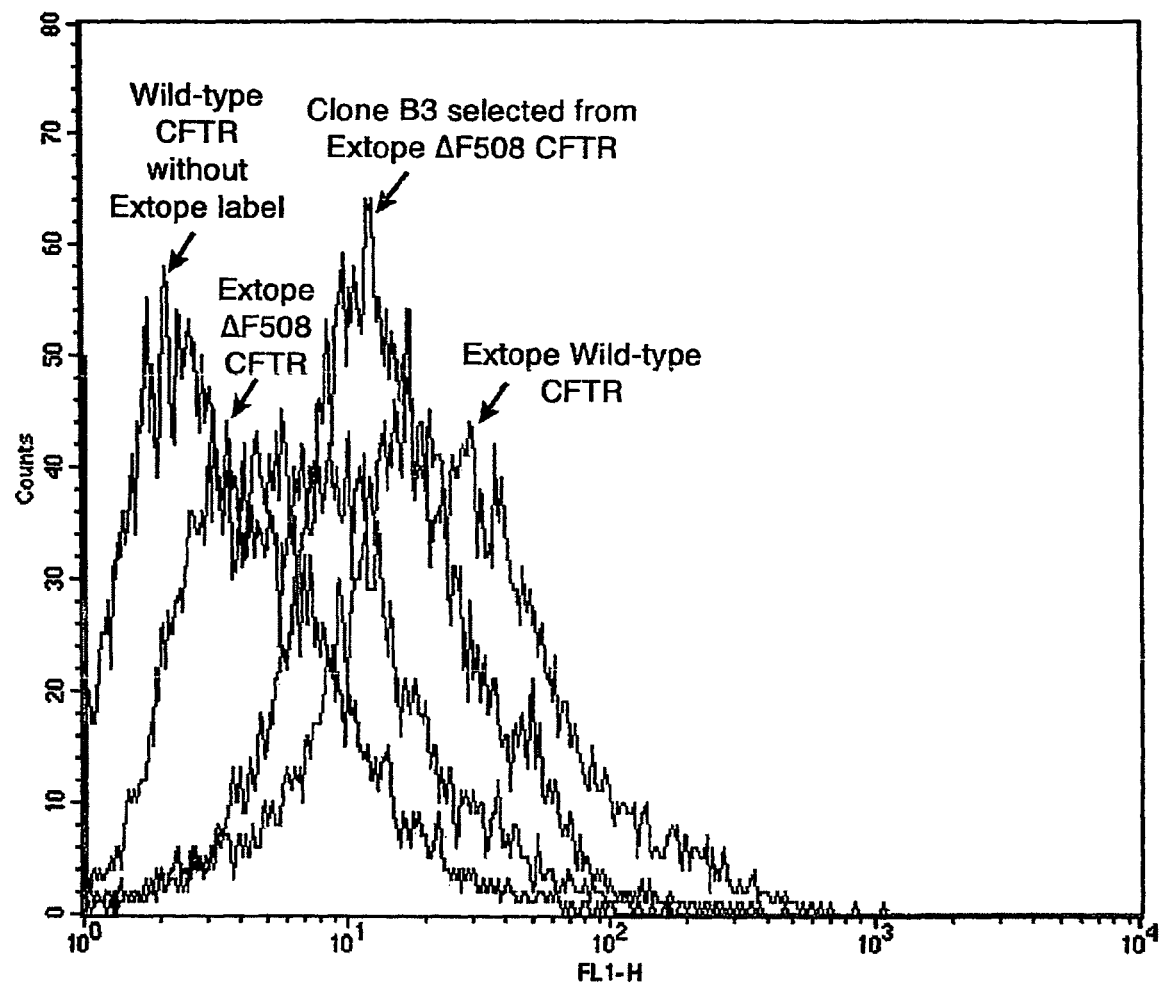
FIG. 7. Selection of cells with XT-ΔF508 CFTR at the surface. Fluorescence activated cell sorting (FACS) of XT-wild type and –ΔF508 CFTR. Repeated selection of clonal populations (eg. Clone B3) from the leading edge of the XT-ΔF508 CFTR fluorescence peak with or without exposure to chemical mutagens yields populations in which sufficient ΔF508 CFTR reaches the cell surface to provide cAMP regulated chloride channel activity.

In addition to this primary purpose the assay has other related applications in the discovery of therapeutic small molecules for treatment of cystic fibrosis. First as shown in FIG. 7 it has become possible to utilize fluorescence activated cell sorting (FACS) to select for clonal subpopulations of ΔF508 CFIR expressing cells in which a genetic change (mutation) has occurred that enables the mutant protein to reach the cell surface. There are reasons to believe that such changes may occur because wild-type CFTR is known to mature to varying extents in different mammalian cell types and because intragenic mutations coding for amino acids in the first nucleotide binding domain of CFTR were found to promote maturation in yeast (Teem et al., 1993). The present assay enables the detection of either intragenic or intergenic suppressor mutations enabling ΔF508 CFTR maturation in mammalian cells. Identification of such mutations will provide additional targets for screening of compounds to overcome the ΔF508 CFTR phenotype.

Figure 8:
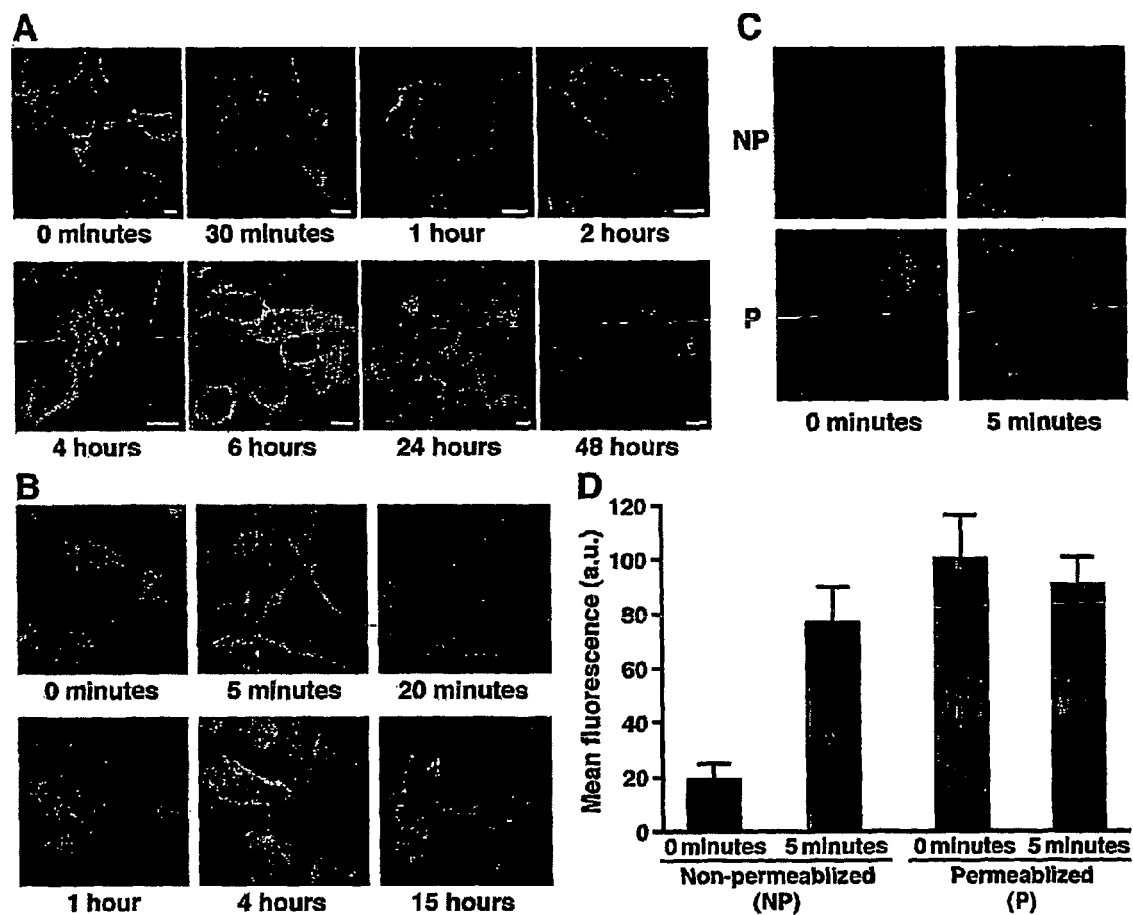
FIG. 8. Extope-CFTR is internalized and recycled.
Figure 9:
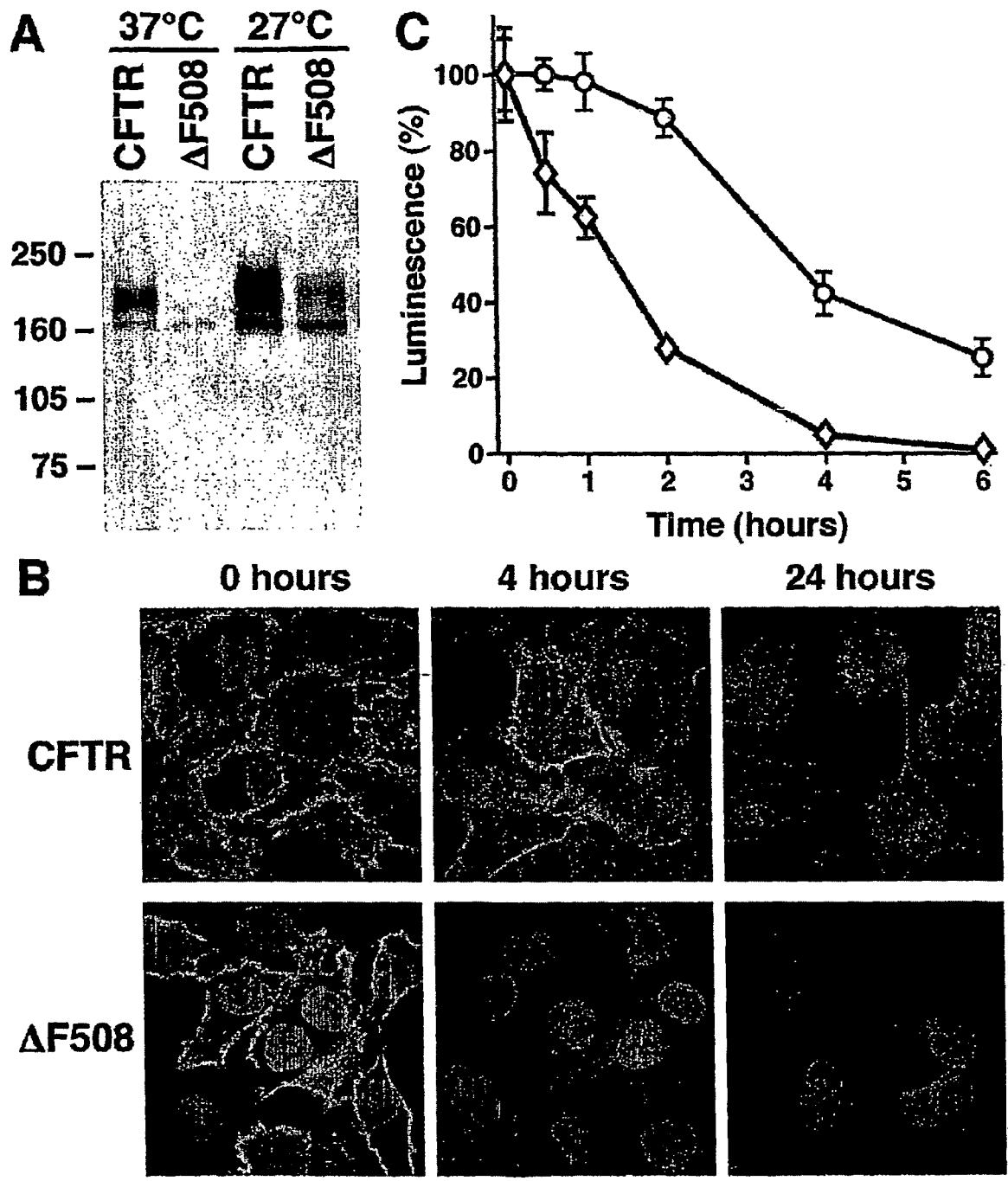
FIG. 9. Detection of accelerated turnover of ΔF508-CFTR at the cell surface.
Figure 10:
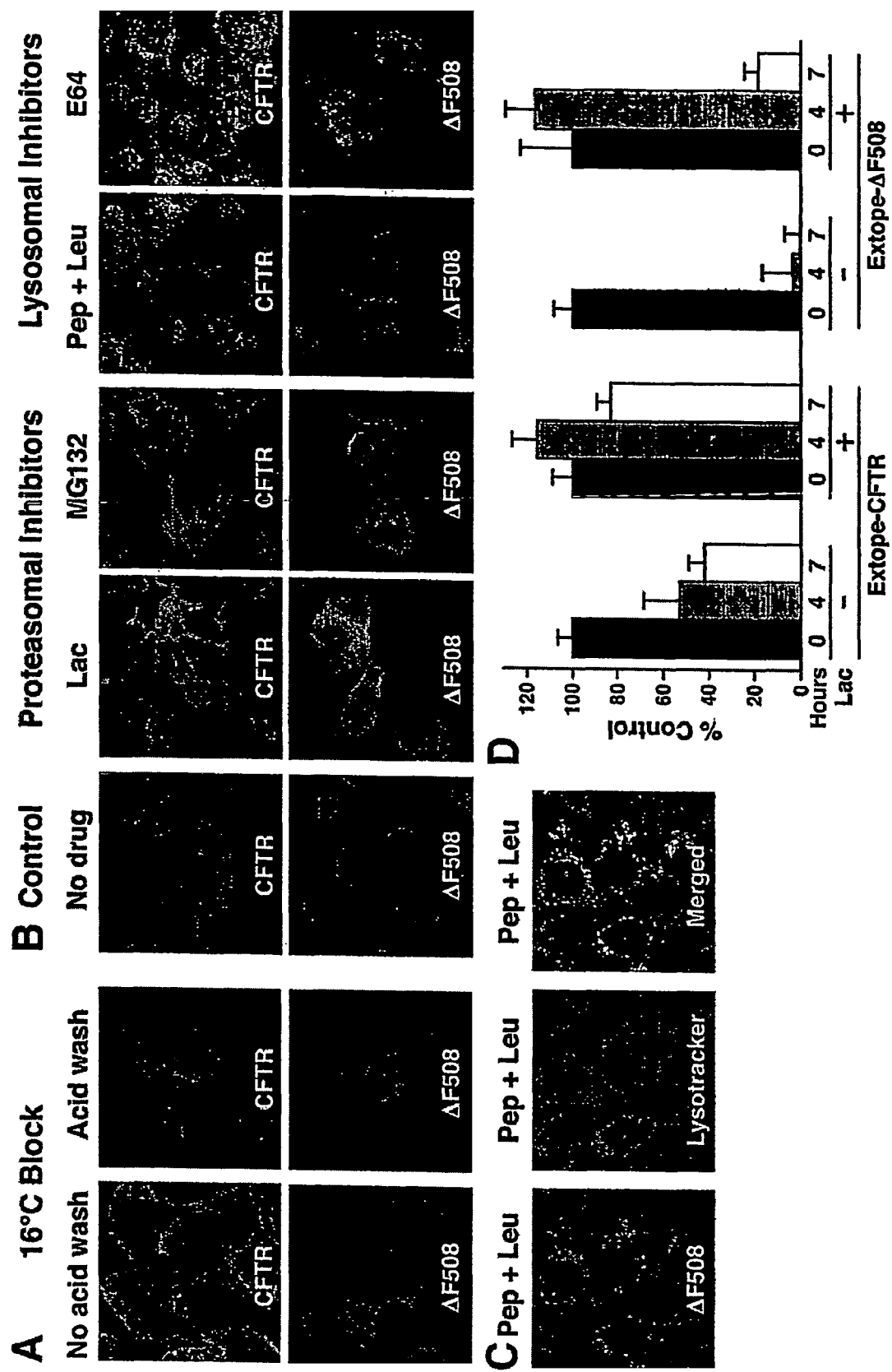
FIG. 10. Stabilization of ΔF508 CFTR by low temperature and protease inhibitors.
Figure 11:
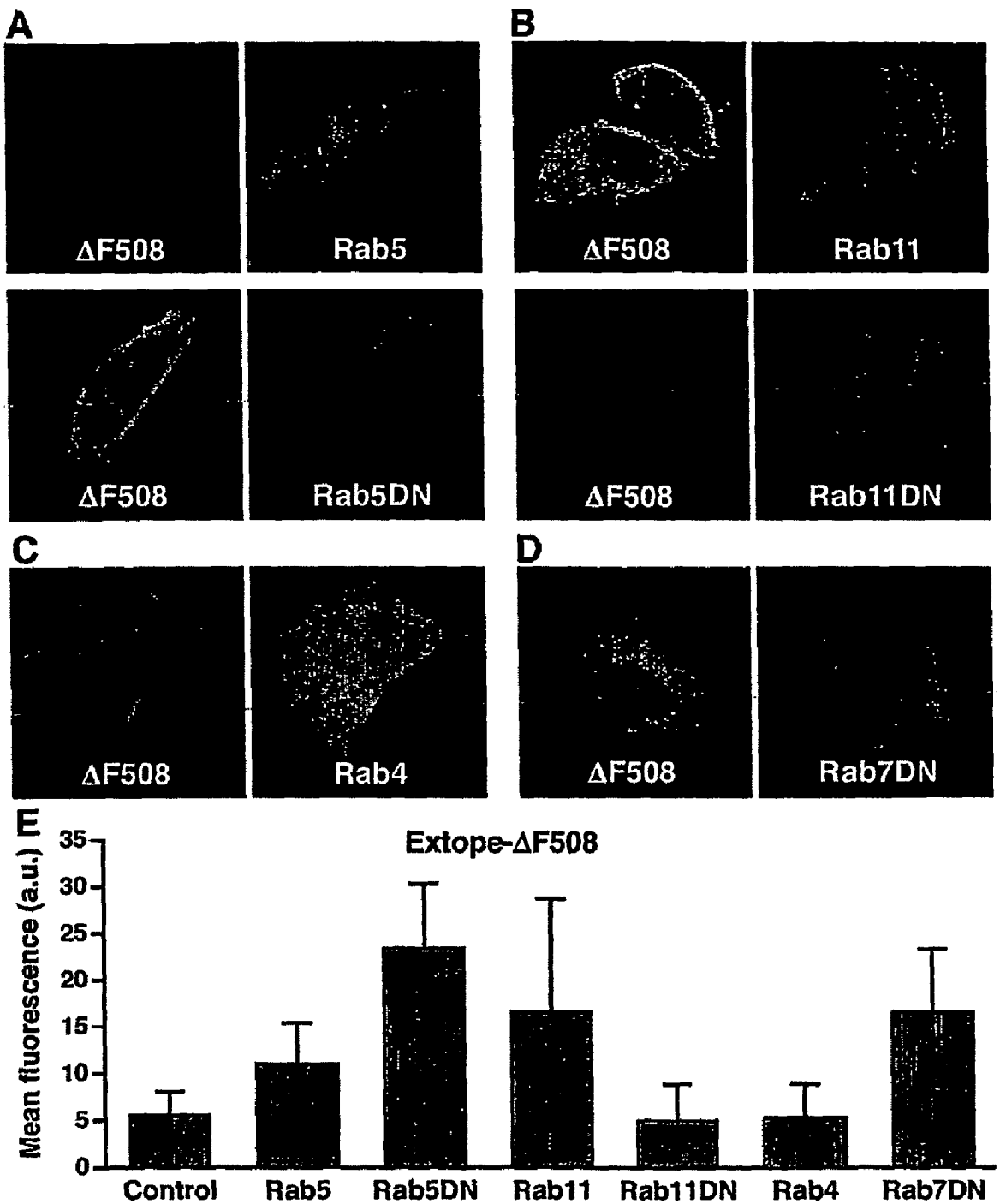
FIG. 11. Rescue of the cell surface pool of ΔF508 CFTR by Rab11 and Rab5DN. Cells were grown at 27° C. in the presence of butyrate and different Rab GTPases were transiently overexpressed as EGFP (Rab4) or DsRed (Rab5, Rab5DN, Rab11, Rab11DN and Rab7DN) fusions. Extope-ΔF508 CFTR was labeled with 16B12 mAb as described in FIG. 6 and detected 24 hours later with goat anti-mouse IgG Alexa Fluor 488 conjugate or goat anti-mouse IgG Alexa Fluor 568 conjugate.

The second additional application of the described method of CFTR detection at the surface of living cells is screening for compounds that slow the turnover of CFTR at the cell surface. FIG. 8 illustrates the use of the assay to observe that wild-type CFTR is rapidly endocytosed from the cell surface followed by a recycling step back to the surface of a portion of the amount taken up. FIG. 9 shows that ΔF508 CFTR is also rapidly removed from the surface but does not return. Therefore it will be desirable to discover agents that can not only promote appearance of ΔF508 and other misprocessed mutants at the cell surface but also stabilize it there. The feasibility of this surface stabilization is demonstrated in FIGS. 10 and 11. The amounts of both wild-type and ΔF508 CFTR at the surface are greatly increased by incubation at low temperature (16° C.) as well as by either proteasomal or lysosomal protease inhibitors (FIG. 10). CFTR is strongly stabilized at the cell surface by genetic manipulations as well (FIG. 11). These experiments show that overexpression of a dominant negative version of the Rab5 GTPase required for the initial endocytic step to early endosomes stabilized surface ΔF508 CFTR as did overexpression of wild-type Rab11 necessary for recycling to the surface. Thus the assay enables screens of small molecules influencing the appearance and stability of ΔF508 CFTR at the surface of cells where it is required for the normal functioning of many epithelial tissues.

REFERENCES

Benharouga, M., M. Sharma, et al. (2003). "The role of the C-terminus and Na+/H+ exchanger regulatory factor (NHERF) in the functional expression of CFTR in non-polarized cells and epithelia." *J. Biol. Chem.*: M301030200.

Chang, X.-B., Tabcharani, J. A., Hou, Y.-X., Jensen, T. J., Kartner, N., Alon, N., Hanrahan, J. W. and Riordan, J. R (1993) Protein kinase A (PKA) still activates CFTR chloride channel after mutagenesis of all 10 PKA consensus phosphorylation sites. J. Biol. Chem. 268(15):11304-11311.

Denning, G. M., L. S. Ostedgaard, et al. (1992). "Abnormal localization of cystic fibrosis transmembrane conductance regulator in primary cultures of cystic fibrosis airway epithelia." *J. Cell Biol.* 118: 551-559.

Drumm, M. L. and F. S. Collins (1993). "Molecular biology of cystic fibrosis." *Mol Genet Med* 3: 33-68.

Gelman, M. S. and R. R. Kopito (2002). "Rescuing protein conformation: prospects for pharmacological therapy in cystic fibrosis." *J Clin Invest* 110(11): 1591-7.

Hou Y X, Cui L, Riordan J R, and Chang X B. (2000). Allosteric interactions between the two non-equivalent nucleotide binding domains of multidrug resistance protein MRP 1. J Biol Chem 275, 20280-20287.

Howard, M., M. D. DuVall, et al. (1995). "Epitope tagging permits cell surface detection of functional CFTR." *Am J Physiol* 269(6 Pt 1): C1565-76.

Howard, M., T. Jilling, et al. (1996). "cAMP-regulated trafficking of epitope-tagged CFTR." *Kidney Int* 49(6): 1642-8.

Konstas, A. A., J. P. Koch, et al. (2002). "Cystic fibrosis transmembrane conductance regulator-dependent up-regulation of Kir1.1 (ROMK) renal K+ channels by the epithelial sodium channel." *J Biol Chem* 277(28): 25377-84.

Kopito, R. R. (1999). "Biosynthesis and degradation of CFTR." *Physiol Rev* 79(1 Suppl): S167-73.

Riordan, J. R. (1999). "Cystic fibrosis as a disease of misprocessing of the cystic fibrosis transmembrane conductance regulator glycoprotein." *Am J Hum Genet* 64(6): 1499-504.

Riordan, J. R., J. M. Rommens, et al. (1989). "Identification of the cystic fibrosis gene: cloning and characterization of complementary DNA." *Science* 245(4922): 1066-73.

Schultz, B. D., A. Takahashi, et al. (1997). "FLAG epitope positioned in an external loop preserves normal biophysical properties of CFTR." *Am J Physiol* 273(6 Pt 1): C2080-9.

Seibert, F. S., T. W. Loo, et al. (1997). "Cystic Fibrosis: Channel, Catalytic, and Folding Properties of the CFTR Protein." *J Bioenerg Biomembr* 29(5): 429-42.

Teem, J. L., Berger, H. A., Ostedgaard, L. S., Rich, D. P., Tsui, L-C., Welsh, M. J. (1993). "Identification of revertants for the cystic fibrosis Delta F508 mutation using STE6-CFTR chimeras in yeast." Cell 73(2): 335-46.

The foregoing is illustrative of the present invention, and is not to be construed as limiting thereof. The invention is defined by the following claims, with equivalents of the claims to be included therein.

That which is claimed is:

1. A recombinant nucleic acid encoding a modified human cystic fibrosis transmembrane conductance regulator (CFTR) protein, wherein said recombinant nucleic acid contains a nucleic acid segment encoding the peptide segment EL2: WELNTSYDPDNKGNTYPYDVPDYAN-SYAYIITSKEERSLQ (SEQ ID NO:23), and wherein said nucleic acid is modified by the insertion of a first heterologous segment encoding a detectable epitope in the region encoding the second extracellular cytoplasmic loop (EL2).

2. The recombinant nucleic acid according to claim 1, wherein said detectable epitope is selected from the group consisting of the influenza hemagluttinin (HA) epitope, the HSV epitope, the T7 Tag epitope, the Flag epitope, the Xpress epitope, the V5 epitope, and the c-myc epitope.

3. The recombinant nucleic acid of claim 1 encoding phenylalanine at position 508 of the encoded CFTR protein.

4. The recombinant nucleic acid of claim 1 encoding a deletion of phenylalanine at position 508 of the encoded CFTR protein.

5. A vector comprising the recombinant nucleic acid of claim 1 operably associated with a promoter.

6. An isolated cell that contains the recombinant nucleic acid of claim 1.

7. The isolated cell of claim 6, wherein said cell is a mammalian cell.

8. A recombinant nucleic acid encoding a modified human cystic fibrosis transmembrane conductance regulator (CFTR) protein, wherein said nucleic acid is modified by the insertion of a first heterologous segment encoding a detectable epitope in the region encoding the second extracellular cytoplasmic loop (EL2) between the regions coding for amino acids W216 and Q220 of the CFTR protein.

9. The recombinant nucleic acid according to claim 8, wherein said detectable epitope is selected from the group consisting of the influenza hemagluttinin (HA) epitope, the HSV epitope, the T7 Tag epitope, the Flag epitope, the Xpress epitope, the V5 epitope, and the c-myc epitope.

10. The recombinant nucleic acid of claim 8 encoding phenylalanine at position 508 of the encoded CFTR protein.

11. The recombinant nucleic acid of claim 8 encoding a deletion of phenylalanine at position 508 of the encoded CFTR protein.

12. A vector comprising the recombinant nucleic acid of claim 8 operably associated with a promoter.

13. An isolated cell that contains the recombinant nucleic acid of claim 8.

* * * * *

UNITED STATES PATENT AND TRADEMARK OFFICE
CERTIFICATE OF CORRECTION

PATENT NO. : 8,076,101 B2
APPLICATION NO. : 10/554770
DATED : December 13, 2011
INVENTOR(S) : Riordan Page 1 of 1

It is certified that error appears in the above-identified patent and that said Letters Patent is hereby corrected as shown below:

In the Specification:
Column 1, Line 22: Please correct "Δ508" to read -- ΔF508 --

Column 13, Line 23: Please correct "ACATCGAAGGAGGACGCAGT/"
to read -- ACATCGAAGGAGGAACGCAGT/ --

Signed and Sealed this
Eleventh Day of June, 2013

Teresa Stanek Rea
*Acting Director of the United States Patent and Trademark Office*

SEQUENCE LISTING

<160> NUMBER OF SEQ ID NOS: 47

<210> SEQ ID NO 1
<211> LENGTH: 11
<212> TYPE: PRT
<213> ORGANISM: Artificial
<220> FEATURE:
<223> OTHER INFORMATION: HSV epitope tag

<400> SEQUENCE: 1

Gln Pro Glu Leu Ala Pro Glu Asp Pro Glu Asp
1               5                   10

```
<210> SEQ ID NO 2
<211> LENGTH: 11
<212> TYPE: PRT
<213> ORGANISM: Artificial
<220> FEATURE:
<223> OTHER INFORMATION: T7 epitope tag

<400> SEQUENCE: 2

Met Ala Ser Met Thr Gly Gly Gln Gln Met Gly
1               5                   10

<210> SEQ ID NO 3
<211> LENGTH: 8
<212> TYPE: PRT
<213> ORGANISM: Artificial
<220> FEATURE:
<223> OTHER INFORMATION: Flag eptiope tag

<400> SEQUENCE: 3

Asp Tyr Lys Asp Asp Asp Asp Lys
1               5

<210> SEQ ID NO 4
<211> LENGTH: 8
<212> TYPE: PRT
<213> ORGANISM: Artificial
<220> FEATURE:
<223> OTHER INFORMATION: Xpress epitope tag

<400> SEQUENCE: 4

Asp Leu Tyr Asp Asp Asp Asp Lys
1               5

<210> SEQ ID NO 5
<211> LENGTH: 14
<212> TYPE: PRT
<213> ORGANISM: Artificial
<220> FEATURE:
<223> OTHER INFORMATION: V5 epitope tag

<400> SEQUENCE: 5

Gly Lys Pro Ile Pro Asn Pro Leu Leu Gly Leu Asp Ser Thr
1               5                   10

<210> SEQ ID NO 6
<211> LENGTH: 10
<212> TYPE: PRT
<213> ORGANISM: Artificial
<220> FEATURE:
<223> OTHER INFORMATION: c-myc epitope tag

<400> SEQUENCE: 6

Glu Gln Lys Leu Ile Ser Glu Glu Asp Leu
1               5                   10

<210> SEQ ID NO 7
<211> LENGTH: 25
<212> TYPE: DNA
<213> ORGANISM: Artificial
<220> FEATURE:
<223> OTHER INFORMATION: Synthetic oligonucleotide

<400> SEQUENCE: 7
agccgtgttc tagataaaat aagta                                           25

<210> SEQ ID NO 8
<211> LENGTH: 30
```

```
<212> TYPE: DNA
<213> ORGANISM: Artificial
<220> FEATURE:
<223> OTHER INFORMATION: Synthetic oligonucleotide

<400> SEQUENCE: 8
gtcatcacca ttagcagttt ttctattgtt                                          30

<210> SEQ ID NO 9
<211> LENGTH: 42
<212> TYPE: DNA
<213> ORGANISM: Artificial
<220> FEATURE:
<223> OTHER INFORMATION: Synthetic oligonucleotide

<400> SEQUENCE: 9
atccgggtca taggaagtat ttaacaactc ccagattagc cc                            42

<210> SEQ ID NO 10
<211> LENGTH: 42
<212> TYPE: DNA
<213> ORGANISM: Artificial
<220> FEATURE:
<223> OTHER INFORMATION: Synthetic oligonucleotide

<400> SEQUENCE: 10
gtatggataa gtattccctt tgttatccgg gtcataggaa gt                            42

<210> SEQ ID NO 11
<211> LENGTH: 42
<212> TYPE: DNA
<213> ORGANISM: Artificial
<220> FEATURE:
<223> OTHER INFORMATION: Synthetic oligonucleotide

<400> SEQUENCE: 11
gttagcgtag tcaggaacgt cgtatggata agtattccct tt                            42

<210> SEQ ID NO 12
<211> LENGTH: 36
<212> TYPE: DNA
<213> ORGANISM: Artificial
<220> FEATURE:
<223> OTHER INFORMATION: Synthetic olignucleotide

<400> SEQUENCE: 12
tcgaaggagg aacgcagttt acaggcgtct gccttc                                   36

<210> SEQ ID NO 13
<211> LENGTH: 36
<212> TYPE: DNA
<213> ORGANISM: Artificial
<220> FEATURE:
<223> OTHER INFORMATION: Synthetic oligonucleotide

<400> SEQUENCE: 13
tacgctgtca tcattacatc gaaggaggaa cgcagt                                   36

<210> SEQ ID NO 14
<211> LENGTH: 42
<212> TYPE: DNA
<213> ORGANISM: Artificial
<220> FEATURE:
<223> OTHER INFORMATION: SYnthetic oligonucleotide

<400> SEQUENCE: 14
gacgttcctg actacgctaa ctcttacgct gtcatcatta ca                            42
```

<210> SEQ ID NO 15
<211> LENGTH: 39
<212> TYPE: DNA
<213> ORGANISM: Artificial
<220> FEATURE:
<223> OTHER INFORMATION: Synthetic oligonucleotide

<400> SEQUENCE: 15
atccgggtca taggaagtat tttctccttc tcctgttgt                    39

<210> SEQ ID NO 16
<211> LENGTH: 39
<212> TYPE: DNA
<213> ORGANISM: Artificial
<220> FEATURE:
<223> OTHER INFORMATION: Synthetic oligonucleotide

<400> SEQUENCE: 16
acatcgaagg aggaacgcag tggaagagtt ggtattatc                    39

<210> SEQ ID NO 17
<211> LENGTH: 22
<212> TYPE: DNA
<213> ORGANISM: Artificial
<220> FEATURE:
<223> OTHER INFORMATION: Synthetic oligonucleotide

<400> SEQUENCE: 17
gccgacactt tgcttgctat gg                                      22

<210> SEQ ID NO 18
<211> LENGTH: 33
<212> TYPE: DNA
<213> ORGANISM: Artificial
<220> FEATURE:
<223> OTHER INFORMATION: Synthetic oligonucleotide

<400> SEQUENCE: 18
tgataacaaa gtactctgcc ctgatccagt tct                          33

<210> SEQ ID NO 19
<211> LENGTH: 15
<212> TYPE: PRT
<213> ORGANISM: Homo sapiens

<400> SEQUENCE: 19

Gly Arg Ile Ile Ala Ser Tyr Asp Pro Asp Asn Lys Glu Glu Arg
1               5                   10                  15

<210> SEQ ID NO 20
<211> LENGTH: 5
<212> TYPE: PRT
<213> ORGANISM: Homo sapiens

<400> SEQUENCE: 20

Trp Glu Leu Leu Gln
1               5

<210> SEQ ID NO 21
<211> LENGTH: 31
<212> TYPE: PRT
<213> ORGANISM: Homo sapiens

<400> SEQUENCE: 21

Leu Trp Leu Leu Gly Asn Thr Pro Leu Gln Asp Lys Gly Asn Ser Thr

```
                1               5                   10                  15
His Ser Arg Asn Asn Ser Tyr Ala Val Ile Ile Thr Ser Thr Ser
                20                  25                  30

<210> SEQ ID NO 22
<211> LENGTH: 5
<212> TYPE: PRT
<213> ORGANISM: Homo sapiens

<400> SEQUENCE: 22

Glu Gly Glu Gly Arg
1               5

<210> SEQ ID NO 23
<211> LENGTH: 40
<212> TYPE: PRT
<213> ORGANISM: Artificial
<220> FEATURE:
<223> OTHER INFORMATION: EL2 loop insertion sequence

<400> SEQUENCE: 23

Trp Glu Leu Asn Thr Ser Tyr Asp Pro Asp Asn Lys Gly Asn Thr Tyr
1               5                   10                  15

Pro Tyr Asp Val Pro Asp Tyr Ala Asn Ser Tyr Ala Tyr Ile Ile Thr
                20                  25                  30

Ser Lys Glu Glu Arg Ser Leu Gln
        35                  40

<210> SEQ ID NO 24
<211> LENGTH: 40
<212> TYPE: PRT
<213> ORGANISM: Artificial
<220> FEATURE:
<223> OTHER INFORMATION: EL6 loop insertion sequence

<400> SEQUENCE: 24

Glu Gly Glu Asn Thr Ser Tyr Asp Pro Asp Asn Lys Gly Asn Thr Tyr
1               5                   10                  15

Pro Tyr Asp Val Pro Asp Tyr Ala Asn Ser Tyr Ala Tyr Ile Ile Thr
                20                  25                  30

Ser Lys Glu Glu Arg Ser Gly Arg
        35                  40

<210> SEQ ID NO 25
<211> LENGTH: 40
<212> TYPE: PRT
<213> ORGANISM: Artificial
<220> FEATURE:
<223> OTHER INFORMATION: EL2 loop insertion sequence with HA epitope tag

<400> SEQUENCE: 25

Trp Glu Leu Asn Thr Ser Tyr Asp Pro Asp Asn Lys Gly Asn Thr Tyr
1               5                   10                  15

Pro Tyr Asp Val Pro Asp Tyr Ala Asn Ser Tyr Ala Tyr Ile Ile Thr
                20                  25                  30

Ser Lys Glu Glu Arg Ser Leu Gln
        35                  40

<210> SEQ ID NO 26
<211> LENGTH: 40
<212> TYPE: PRT
<213> ORGANISM: Artificial
<220> FEATURE:
<223> OTHER INFORMATION: EL6 loop insertion sequence with HA epitope tag
```

```
<400> SEQUENCE: 26

Glu Gly Glu Asn Thr Ser Tyr Asp Pro Asp Asn Lys Gly Asn Thr Tyr
1               5                   10                  15
Pro Tyr Asp Val Pro Asp Tyr Ala Asn Ser Tyr Ala Val Ile Ile Thr
            20                  25                  30
Ser Lys Glu Glu Arg Ser Gly Arg
        35                  40

<210> SEQ ID NO 27
<211> LENGTH: 6
<212> TYPE: PRT
<213> ORGANISM: Artificial
<220> FEATURE:
<223> OTHER INFORMATION: Inserted EL1 sequence

<400> SEQUENCE: 27

Ser Tyr Asp Pro Asp Asn
1               5

<210> SEQ ID NO 28
<211> LENGTH: 4
<212> TYPE: PRT
<213> ORGANISM: Artificial
<220> FEATURE:
<223> OTHER INFORMATION: Inserted EL1 sequence

<400> SEQUENCE: 28

Lys Glu Glu Arg
1

<210> SEQ ID NO 29
<211> LENGTH: 4
<212> TYPE: PRT
<213> ORGANISM: Artificial
<220> FEATURE:
<223> OTHER INFORMATION: Inserted EL4 sequence

<400> SEQUENCE: 29

Lys Gly Asn Thr
1

<210> SEQ ID NO 30
<211> LENGTH: 9
<212> TYPE: PRT
<213> ORGANISM: Artificial
<220> FEATURE:
<223> OTHER INFORMATION: Inserted EL4 sequence

<400> SEQUENCE: 30

Asn Ser Tyr Ala Tyr Ile Ile Thr Ser
1               5

<210> SEQ ID NO 31
<211> LENGTH: 9
<212> TYPE: PRT
<213> ORGANISM: Artificial
<220> FEATURE:
<223> OTHER INFORMATION: HA epitope tag

<400> SEQUENCE: 31

Tyr Pro Tyr Asp Val Pro Asp Tyr Ala
1               5

<210> SEQ ID NO 32
<211> LENGTH: 13
```

```
<212> TYPE: PRT
<213> ORGANISM: Artificial
<220> FEATURE:
<223> OTHER INFORMATION: EL2 loop insertion sequence

<400> SEQUENCE: 32

Gly Leu Ile Trp Glu Leu Asn Thr Ser Tyr Asp Pro Asp
1               5                   10

<210> SEQ ID NO 33
<211> LENGTH: 14
<212> TYPE: PRT
<213> ORGANISM: Artificial
<220> FEATURE:
<223> OTHER INFORMATION: EL2 loop insertion sequence

<400> SEQUENCE: 33

Thr Ser Tyr Asp Pro Asp Asn Lys Gly Asn Thr Tyr Pro Tyr
1               5                   10

<210> SEQ ID NO 34
<211> LENGTH: 14
<212> TYPE: PRT
<213> ORGANISM: Artificial
<220> FEATURE:
<223> OTHER INFORMATION: EL2 loop insertion sequence

<400> SEQUENCE: 34

Gly

```
<220> FEATURE:
<223> OTHER INFORMATION: EL6 loop insertion sequence

<400> SEQUENCE: 38

Thr Thr Gly Glu Gly Glu Asn Thr Ser Tyr Asp Pro Asp
1               5                   10

<210> SEQ ID NO 39
<211> LENGTH: 13
<212> TYPE: PRT
<213> ORGANISM: Artificial
<220> FEATURE:
<223> OTHER INFORMATION: EL6 loop insertion sequence

<400> SEQUENCE: 39

Thr Ser Tyr Asp Pro Asp Asn Lys Gly Asn Thr Tyr Pro
1               5                   10

<210> SEQ ID NO 40
<211> LENGTH: 14
<212> TYPE: PRT
<213> ORGANISM: Artificial
<220> FEATURE:
<223> OTHER INFORMATION: EL6 loop insertion sequence

<400> SEQUENCE: 40

Lys Gly Asn Thr Tyr Pro Tyr Asp Val Pro Asp Tyr Ala Asn
1               5                   10

<210> SEQ ID NO 41
<211> LENGTH: 14
<212> TYPE: PRT
<213> ORGANISM: Artificial
<220> FEATURE:
<223> OTHER INFORMATION: EL6 loop insertion sequence

<400> SEQUENCE: 41

Tyr Asp Val Pro Asp Tyr Ala Asn Ser Tyr Ala Tyr Ile Ile
1               5                   10

<210> SEQ ID NO 42
<211> LENGTH: 13
<212> TYPE: PRT
<213> ORGANISM: Artificial
<220> FEATURE:
<223> OTHER INFORMATION: EL6 loop insertion sequence

<400> SEQUENCE: 42

Asn Ser Tyr Ala Tyr Ile Ile Thr Ser Lys Glu Glu Arg
1               5                   10

<210> SEQ ID NO 43
<211> LENGTH: 13
<212> TYPE: PRT
<213> ORGANISM: Artificial
<220> FEATURE:
<223> OTHER INFORMATION: EL6 loop insertion sequence

<400> SEQUENCE: 43

Thr Ser Lys Glu Glu Arg Ser Gly Arg Val Gly Ile Ile
1               5                   10

<210> SEQ ID NO 44
<211> LENGTH: 42
<212> TYPE: DNA
<213> ORGANISM: Artificial
<220> FEATURE:
<223> OTHER INFORMATION: Synthetic oligonucleotide
```

```
<400> SEQUENCE: 44
gggctaatct gggagttgtt aaatacttcc tatgacccgg at                42

<210> SEQ ID NO 45
<211> LENGTH: 42
<212> TYPE: DNA
<213> ORGANISM: Artificial
<220> FEATURE:
<223> OTHER INFORMATION: Synthetic oligonucleotide

<400> SEQUENCE: 45
acttcctatg acccggataa caaagggaat acttatccat ac                42

<210> SEQ ID NO 46
<211> LENGTH: 42
<212> TYPE: DNA
<213> ORGANISM: Artificial
<220> FEATURE:
<223> OTHER INFORMATION: Synthetic oligonucleotide

<400> SEQUENCE: 46
aaagggaata cttatccata cgacgttcct gactacgcta ac                42

<210> SEQ ID NO 47
<211> LENGTH: 39
<212> TYPE: DNA
<213> ORGANISM: Artificial
<220> FEATURE:
<223> OTHER INFORMATION: Synthetic oligonucleotide

<400> SEQUENCE: 47
acaacaggag aaggagaaaa tacttcctat gacccggat                    39
```